United States Patent
Zimmerman et al.

(10) Patent No.: US 6,479,514 B1
(45) Date of Patent: Nov. 12, 2002

(54) QUINOLINE-AMINOMETHYL-PYRIDYL DERIVATIVES WITH ANTI-HELICOBACTER ACTIVITY

(75) Inventors: Peter Zimmerman, Allensbach (DE); Gerhard Grundler, Constance (DE)

(73) Assignee: Altana Pharma AG, Constance (DE)

( * ) Notice: Subject to any disclaimer, the term of this patent is extended or adjusted under 35 U.S.C. 154(b) by 0 days.

(21) Appl. No.: 09/700,682

(22) PCT Filed: May 20, 1999

(86) PCT No.: PCT/EP99/03480

§ 371 (c)(1),
(2), (4) Date: Nov. 17, 2000

(87) PCT Pub. No.: WO99/61438

PCT Pub. Date: Dec. 2, 1999

(30) Foreign Application Priority Data

May 23, 1998 (EP) ............................................. 98109524

(51) Int. Cl.[7] ...................... A61K 31/47; A61K 31/445; C07D 213/00; C07D 215/00; C07D 233/00
(52) U.S. Cl. ...................... 514/313; 514/314; 514/256; 514/269; 514/323; 544/242; 544/333; 544/335; 546/1; 546/135; 546/159; 546/229; 548/225; 548/226; 548/300.1; 548/311.1; 549/29; 549/54; 549/78; 549/83
(58) Field of Search ............................ 546/1, 159, 135, 546/229; 544/333, 242, 335; 514/313, 256, 314, 269, 323; 548/225, 226, 300.1, 311.1; 549/29, 59, 78, 83

(56) References Cited

U.S. PATENT DOCUMENTS 6,395,732 B1   5/2002   Zimmerman et al. ..... 514/227.8

FOREIGN PATENT DOCUMENTS

| EP | 0 246 126 | 4/1987 |
| EP | 0 234 690 | 5/1991 |
| EP | 0 330 485 | 5/1993 |
| EP | 9602505 | * 2/1996 |
| WO | WO 94/10164 | 11/1994 |
| WO | WO 95/28929 | 11/1995 |
| WO | WO 95/34554 | 12/1995 |
| WO | WO 96/02505 | 2/1996 |
| WO | WO 98/04529 | 2/1998 |

OTHER PUBLICATIONS

S. Piras et al., "Quinoxaline Chemistry, Part 6 . . . " *Farmaco* vol. 51, No. 08/09, 1996, pp. 569–577.

Fioravanti et al. IL Farm. 51/10.5463–652 (1996); Synth. & Microbiol. evaln. of N–Hetrocryl–arylmethanamines . . .*

Fioravanti, R. et al., "Synthesis and Microbiological evaluations of (N–Heteroaryl) Arylmethanamines and Their Schiff Bases", *Farmaco*, vol. 51, No. 10, pp. 643–652 (1996).

Ballistreri, A. et al., "Design Synthesis and Antimycotic Activity of (N–Heteroaryl) Arylmethanamines" J. Phys. Org. Chem. vol. 9, No. 2, pp. 61–65 (1996).

Piras, S. et al., "Quinoxaline Chemistry. Part 6–Synthesis and Evaluation of Antiulcer and Gastroprotective Activity of 2–{Arylmethylmercapto–, Arylmethylsulfinyl–, Piperazinyl–, Piperazinyl–3–R–Substituted} Quinoxalines" *Farmaco*, vol. 51, No. 08/09, pp. 569–577 (1996).

Fioravanti, R. et al., "Research on antibacterial and antifungal agents. XI Synthesis and antimicrobial activity of N–heteroaryl benzylamines and their Schiff bases" *Eur J Med Chem.*, vol. 30, No. 2, pp. 123–132 (1995).

* cited by examiner

Primary Examiner—Richard L. Raymond
Assistant Examiner—Sudhaker B. Patel
(74) Attorney, Agent, or Firm—Nath & Associates PLLC; Gary M. Nath; Todd L. Juneau

(57) ABSTRACT

Compounds of formula (I) in which the substituents and symbols have the meanings indicated in the description, are suitable for the control of Helicobacter bacteria.

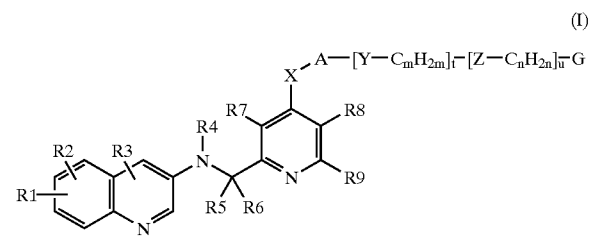

10 Claims, No Drawings

QUINOLINE-AMINOMETHYL-PYRIDYL DERIVATIVES WITH ANTI-HELICOBACTER ACTIVITY

FIELD OF APPLICATION OF THE INVENTION

The invention relates to compounds which are intended to be used in the pharmaceutical industry as active compounds for the production of medicaments.

1. Prior Art

International Patent Applications WO 94/13290, 94/19346, 95/01351, 95/15324, 96/00224, 95/34554, 95/34553, 96/02534 and 96/02505 describe benzimidazole and imidazopyridine derivatives which are said to be suitable for the control of Helicobacter bacteria.

2. Description of the Invention

The invention relates to compounds of the formula I (I)

[structure]

in which

R1, R2 and R3 are identical to or different from one another and are hydrogen, 1–4C-alkyl, 1–4C-alkoxy, hydroxyl, halogen, carboxyl or 1–4C-alkylthio, R4 is hydrogen or 1–4C-alkyl, R5 is hydrogen or 1–4C-alkyl, R6 is hydrogen or 1–4C-alkyl, R7 is hydrogen, 1–4C-alkyl, 1–4C-alkoxy or halogen, R8 is hydrogen, 1–4C-alkyl, 1–4C-alkoxy or halogen, R9 is hydrogen or 14C-alkyl, A is 1–7C-alkylene, 2–7C-alkenylene, 3–7C-cycloalkylene or phenylene, G is hydrogen, 1–7C-alkyl, 1–4C-alkyl which is completely or mainly substituted by fluorine, 2–7C-alkenyl, 3–7C-cycloalkyl, a mono- or di-1–4C-alkylcarbamoyl or -thiocarbamoyl radical, an N-1–4C-alkyl-N'-cyanoamidino radical, a 1-N-1–4C-alkylamino-2-nitroethylene radical, an N-2-propynyl-N'-cyanoamidino radical, an aminosulfonylamidino radical, the radical —N(R10)R11, the part of the compound of the above formula I bonded to A (including X and via X) or a cyclic system or bicyclic system which is unsubstituted or substituted by R12 and R13 and which is selected from the group consisting of benzene, naphthalene, furan, thiophene, pyrrole, oxazole, oxazoline, oxazolidinone, isoxazole, thiazole, thiazoline, isothiazole, imidazole, imidazoline, pyrazole, triazole, tetrazole, thiadiazole, thiadiazole 1-oxide, oxadiazole, pyridine, pyridine N-oxide, pyrimidine, halopyrimidine, piperidine, triazine, pyridone, benzimidazole, imidazopyridine, benzothiazole, benzoxazole, quinoline and imidazopyridazine, in which R10 is 1–7C-alkyl, 3–7C-cycloalkyl or Ar-1–4C-alkyl and R11 is 1–7C-alkyl, 3–7C-cycloalkyl or Ar-1–4C-alkyl, where Ar is phenyl, furyl, naphthyl, tetrahydronaphthyl or phenyl which is substituted by R14, R15 and R16, or in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino radical is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino radical can be substituted in the 2-, 3-, 5- or 6-position by a 1–4C-alkyl radical, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl, a substituted morpholino radical is substituted by one or two identical or different 1–4C-alkyl radicals, a substituted thiomorpholino radical is substituted by one or two identical or different 1–4C-alkyl radicals or a carboxyl group, a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C-alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 3–7C-cycloalkyl, 1–4C-alkoxy, carboxyl, 1–4C-alkoxycarbonyl, pyridinyl or —N(R18)R19, where
R18 is hydrogen, 1–4C-alkyl or —CO—R20 and
R19 is hydrogen or 1–4C-alkyl,
or where
R18 and R19, together and including the nitrogen atom to which both are bonded, are a piperidino or morpholino radical,
R20 is hydrogen, 1–4C-alkyl or 1–4C-alkoxy,
X is O (oxygen), N-1–4C-alkyl, NH or S,
Y is O (oxygen), N-1–4C-alkyl, NH, S, 1,4-piperazinylene or 1,4-piperidinylene,
Z is O (oxygen), N-1–4C-alkyl, NH or S or CO,
m is a number from 1 to 7,
n is a number from 0 to 4,
t is the number 0 or 1 and
u is the number 0 or 1,
and their salts.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-Alkoxy represents a radical which, in addition to the oxygen atom, contains one of the abovementioned 1–4C-alkyl radicals. Examples which may be mentioned are the methoxy and the ethoxy radicals.

Halogen within the meaning of the present invention is bromine, chlorine or fluorine.

1–4C-Alkylthio represents a radical which, in addition to the sulfur atom, contains one of the abovementioned 1–4C-alkyl radicals. Examples which may be mentioned are the methylthio and the ethylthio radicals.

1–7C-Alkylene represents straight-chain or branched 1–7C-alkylene radicals, for example the methylene (—CH$_2$—), ethylene (—CH$_2$—CH$_2$—), trimethylene (—CH$_2$—CH$_2$—CH$_2$—), tetra-methylene (—CH$_2$—CH$_2$—CH$_2$—), 1,2-dimethylethylene [—CH(CH$_3$)—CH(CH$_3$)—], 1,1-dimethylethylene [—C(CH$_3$)$_2$—CH$_2$—], 2,2-dimethylethylene [—CH$_2$—C(CH$_3$)$_2$—], isopropylidene [—C(CH$_3$)$_2$—], 1-methylethylene [—CH(CH$_3$)—CH$_2$—], pentamethylene (—CH$_2$—CH$_2$—CH$_2$—CH$_2$—CH$_2$—), hexamethylene (—CH$_2$—CH$_2$—CH$_2$—CH$_2$—CH$_2$—CH$_2$—) and the heptamethylene (—CH$_2$—CH$_2$—CH$_2$—CH$_2$—CH$_2$—CH$_2$—CH$_2$—) radicals. When t is the number 1 or t is the number 0 and at the same time u is the number 1, A preferably has the meaning 2–7C-alkylene. Of the alkylene radicals A, the ethylene, the propylene and the butylene radicals are preferred.

2–7C-Alkenylene represents straight-chain or branched 2–7C-alkenylene radicals, under which is understood a mono- or polyunsaturated divalent hydrocarbon radical. Examples which may be mentioned are the vinylene (—CH=CH—), 1-propenylene (—CH=CH—CH$_2$—), 2-butenylene (—CH$_2$—CH=CH—CH$_2$—) and the 1,3-butadienylene (—CH=CH—CH=CH—) radicals.

3–7C-Cycloalkyl represents cyclopropyl, cyclobutyl, cyclopentyl, cyclohexyl and cycloheptyl.

3–7C-Cycloalkylene represents one of the abovementioned 3–7C-cycloalkyl radicals having two bonds. An example which may be mentioned is the 1,4-cyclohexylene radical.

Phenylene represents the 1,2-, 1,3- and 1,4-phenylene radicals, of which the 1,4-phenylene radical is preferred.

1–7C-Alkyl represents straight-chain or branched alkyl radicals having 1 to 7 carbon atoms. Examples which may be mentioned are the heptyl, isoheptyl, (5-methylhexyl), hexyl, isohexyl (4-methylpentyl), neohexyl (3,3-dimethylbutyl), pentyl, isopentyl-(3-methylbutyl), neopentyl (2,2-dimethylpropyl), butyl, iso-butyl, sec-butyl, tert-butyl, propyl, isopropyl, ethyl and methyl radicals.

Examples of 1–4C-alkyl which is completely or mainly substituted by fluorine are the 2,2,3,3,3-pentafluoropropyl, the perfluoroethyl and the 1,2,2-trifluoroethyl radicals, in particular the 1,1,2,2-tetrafluoroethyl, the 2,2,2-trifluoroethyl, the trifluoromethyl and the difluoromethyl radicals.

2–7C-Alkenyl represents straight-chain or branched alkenyl radicals having 2 to 7 carbon atoms. Examples which may be mentioned are the 2-butenyl, 3-butenyl, 1-propenyl, 2-propenyl (allyl) and vinyl radicals.

Mono- or di-1–4C-alkylcarbamoyl radicals are carbamoyl radicals (—CO—NH$_2$) which are substituted by one or two identical or different 1–4C-alkyl radicals from those mentioned above. Examples which may be mentioned are the methylcarbamoyl, the isopropylcarbamoyl and the dimethylcarbamoyl radicals.

Mono- or di-1–4C-alkylthiocarbamoyl radicals are thiocarbamoyl radicals (—CS—NH$_2$) which are substituted by one or two identical or different 1–4C-alkyl radicals from those mentioned above. Examples which may be mentioned are the methylthiocarbamoyl, the isopropylthiocarbamoyl and the dimethylthiocarbamoyl radicals.

An example of an N-1–4C-alkyl-N'-cyanoamidino radical which may be mentioned is in particular the N-methyl-N'-cyanoamidino radical [—C(=NCN)—NH—CH$_3$].

An example of a 1-N-1–4C-alkylamino-2-nitroethylene radical which may be mentioned is in particular the 1-N-methylamino-2-nitroethylene radical [—C(NHCH$_3$)=CHNO$_2$].

Exemplary radicals —[Z—C$_n$H$_{2n}$]$_u$—G where G=an N-1–4C-alkyl-N'-cyanoamidino radical, 1-N-1–4C-alkylamino-2-nitroethyl radical or N-2-propynyl-N'-cyanoamidino radical to be mentioned are in particular those radicals in which Z has the meaning NH and n is the number 0. In this connection, radicals —[Z—C$_n$H$_{2n}$]$_u$—G particularly to be mentioned are the radicals —NH—C(=NCN) NH—CH$_3$, —NH—C(NHCH$_3$)=CHNO$_2$ and —NH—C(=NCN)NH—CH$_2$C=CH.

1–4C-Alkoxy-1–4C-alkyl represents one of the abovementioned 1–4C-alkyl radicals which is substituted by one of the abovementioned 1–4C-alkoxy radicals. Examples which may be mentioned are the methoxymethyl radical, the methoxyethyl radical and the butoxyethyl radical.

1–4C-Alkoxycarbonyl represents a carbonyl group to which one of the abovementioned 1–4C-alkoxy radicals is bonded. Examples which may be mentioned are the methoxycarbonyl (CH$_3$O—C(O)—) and the ethoxycarbonyl (CH$_3$CH$_2$O—C(O)—) radicals.

In addition to the oxygen atom, 1–4C-alkoxycarbonyloxy radicals contain one of the abovementioned 1–4C-alkylcarbonyl radicals. An example which may be mentioned is the acetoxy radical (CH$_3$CO—O—).

Hydroxy-1–4C-alkyl represents abovementioned 1–4C-alkyl radicals which are substituted by a hydroxyl group. Examples which may be mentioned are the hydroxymethyl, the 2-hydroxyethyl and the 3-hydroxypropyl radicals.

3–7C-Cycloalkyl-1–4C-alkyl represents one of the abovementioned 1–4C-alkyl radicals which is substituted by one of the abovementioned 3–7C-cycloalkyl radicals. Examples which may be mentioned are the cyclopropylmethyl, the cyclohexylmethyl and the cyclohexylethyl radicals.

1–4C-Alkoxycarbonyl-1–4C-alkyl represents one of the abovementioned 1–4C-alkyl radicals which is substituted by one of the abovementioned 1–4C-alkoxycarbonyl radicals. An example which may be mentioned is the ethoxycarbonylmethyl radical ($CH_3CH_2OC(O)CH_2$—).

Phenyl-1–4C-alkyl represents one of the abovementioned 1–4C-alkyl radicals which is substituted by phenyl. Examples which may be mentioned are the phenethyl and the benzyl radicals.

Exemplary 1–4C-alkyl radicals substituted by R17 which may be mentioned are the 2-methoxycarbonylethyl, the 2-ethoxycarbonylethyl, the methoxycarbonylmethyl, the carboxymethyl, the 2-hydroxyethyl, the methoxymethyl, the 2-methoxyethyl, the 2-hydroxyethyl, the dimethylaminomethyl and the 2-dimethylaminoethyl radicals and, in particular, the cyclopropylmethyl and the pyridin4-ylmethyl radicals.

Possible radicals —$C_mH_{2m}$— are straight-chain or branched radicals. Examples which may be mentioned are the heptylene, isoheptylene (2-methylhexylene), hexylene, isohexylene (2-methylpentylene), neohexylene (2,2-dimethylbutylene), pentylene, isopentylene (3-methylbutylene), neopentylene (2,2-dimethylpropylene), butylene, isobutylene, sec-butylene, tert-butylene, propylene, isopropylene, ethylene and methylene radicals. Radicals —$C_mH_{2m}$— preferably to be mentioned are the methylene (—$CH_2$—), the ethylene (—$CH_2CH_2$—), the butylene (—$CH_2CH_2CH_2CH_2$—) and the propylene (—$CH_2CH_2CH_2$—) radicals.

Possible radicals —$C_nH_{2n}$— are likewise straight-chain or branched radicals. Examples which may be mentioned are the butylene, iso-butylene, sec-butylene, tert-butylene, propylene, isopropylene, ethylene and methylene radicals. Radicals —$C_nH_{2n}$— preferably to be mentioned are the methylene (—$CH_2$—) and ethylene (—$CH_2CH_2$—) radicals.

In one embodiment, n is the number 0 so that (with the condition that u is the number 1) the expression —$C_nH_{2n}$— is a bonding dash and the radical G is bonded directly to the group Z. This embodiment relates to those compounds in which G is hydrogen or a radical which is bonded to Z via a carbon atom.

In a further embodiment t is the number 0, so that the expression Y—$C_mH_{2m}$ is a bonding dash.

In a further embodiment u is the number 0, so that the expression Z—$C_nH_{2n}$ is a bonding dash.

The person skilled in the art is aware on account of his/her expert knowledge that certain combinations and conformations of X, A, Y, Z, G, m, n, t and u would lead to chemically less stable compounds. This applies in particular to those compounds in which two hetero-atoms (S, O or N) would directly meet or would only be separated by one carbon atom. Those compounds according to the invention which do not have the abovementioned conformations are therefore preferred.

The substituents R12 and R13 can be bonded to the cyclic systems or bicyclic systems G in any conceivable position, it being possible for the substituted or unsubstituted cyclic systems or bicyclic systems G themselves to be linked to the remainder of the molecule in any conceivable position. Exemplary radicals G which may be mentioned which are unsubstituted or substituted by R12 and R13 are: phenyl, 4-methylphenyl, 3-dimethylaminomethylphenyl, 3-piperidinomethylphenyl, 3-carboxymethylphenyl, 2-dimethylaminomethyl-5-methyl-3-furyl, pyrrol-1-yl, 1-methylpyrrol-3-yl, 4,5-dimethyloxazol-2-yl, 3,5-dimethylisoxazol-4-yl, 4,5-dimethylthiazol-2-yl, 4-methyl-5-carboxymethylthiazol-2-yl, 1-methylimidazol-2-yl, 1-methylpyrazol-3-yl, 1-(2-dimethylaminoethyl)pyrazol-3-yl, 5-methyl-1,3,4-oxa diazol-2-yl, 1,2,4-triazol-1-yl, 1,2,4-triazol-2-yl, 1-methyl-1,2,3-triazol-4-yl, 1-methyl-1,2,4-triazol-3-yl, 1-(2-dimethylaminoethyl)-1,2,3-triazol-4-yl, 1-methyltetrazol-5-yl, 1-(2-dimethylaminoethyl)tetrazol-5-yl, 1-carboxymethyltetrazol-5-yl, 5-methyl-1,3,4-thiadiazol-2-yl, 5-trifluoromethyl-1,3,4-thiadiazol-2-yl 1-(2-hydroxyethyl)tetrazol-5-yl, 2-amino-1,3,4-thiadiazol-2-yl, 3-amino-1,2,4-triazol-5-yl, 4-methyl-5-trifluoromethyl-1,2,4-triazol-3-yl, 4-aminopyrimidin-2-yl, 2-furyl, 3-furyl, 3-methyl-2-furyl, 2-methyl-3-furyl, 5-methyl-2-furyl, 5-ethyl-2-furyl, 3-methoxy-2-furyl, 5-dimethylaminomethyl-2-furyl, 5-N-morpholinomethyl-2-furyl, 5-methoxymethyl-2-furyl, 5-hydroxymethyl-2-furyl, 5-N-piperidinomethyl-2-furyl, 5-chloro-2-furyl, 5-fluoro-2-furyl, 2-thienyl, 3-thienyl, 5-methyl-2-thienyl, 5-chloro-2-thienyl, 3-methyl-2-thienyl, 3-amino-2-thienyl, 3-guanidino-2-thienyl, 3-methoxy-2-thienyl, 2-methyl-3-thienyl, 5-dimethylaminomethyl-2-thienyl, 5-N-morpholinomethyl-2-thienyl, 5-methyl-2-pyrrolyl, 2,5-dimethyl-1-pyrrolyl, 1,5-dimethyl-2-pyrrolyl, 1-methyl-2-pyrrolyl, 2-thiazolyl, 4-thiazolyl, 5-thiazolyl, 2-amino-4-thiazolyl, 2-methyl-4-thiazolyl, 2-amino-5-methyl-4-thiazolyl, 4-methyl-5-thiazolyl, 2-dimethylaminomethyl-4-thiazolyl, 2-guanidino-4-thiazolyl, 2-formylamino-4-thiazolyl, 2-N-morpholinomethyl-4-thiazolyl, 4-methyl-5-oxazolyl, 3-guanidino-1-pyrazolyl, 3-guanidino-4-pyrazolyl, 1-imidazolyl, 2-imidazolyl, 4-imidazolyl, 2-methyl-4-imidazolyl, 5-methyl-4-imidazolyl, 2-methyl-1-imidazolyl, 2-methyl-5-nitro-1- imidazolyl, 4,5-dimethyl-2-imidazolyl, 4-hydroxymethyl-5-methyl-1-imidazolyl, 3-methyl-1-pyrazolyl, 5-amino-1,2,4-thiadiazol-3-yl, 4-methoxy-2-pyridinyl, 4-methoxy-3-methyl-2-pyridinyl, 4-pyridinyl, 2-pyrimidinyl, 5-chloro-4-pyrimidinyl, 5-chloro-2,6-dimethyl-4-pyrimidinyl, 2-nitro-1-imidazolyl, 3,4-dimethoxypyridinyl, 1H-benzimidazol-2-yl, 6-imidazof[1,2-b]pyridazinyl and 3-nitro-6-imidazo[1,2-b]-pyridazinyl.

Exemplary phenyl radicals which may be mentioned which are substituted by R14, R15 and R16 are the radicals 3,4-dihydroxy, 3-hydroxy-4-methoxy, 3,4-dimethoxy, 2-methoxy, 2-ethoxy, 3-methoxy, 4-methoxy, 2-hydroxy, 3-hydroxy, 4-hydroxy, 3,4-dihydroxy, 4-acetyl, 4-fluoro, 4-chloro, 2-chloro, 3-chloro, 3,4-dichloro, 3-trifluoromethyl, 2-trifluoromethyl, 2-methyl, 3-methyl, 4-methyl, 2,3-dimethyl, 2,4-dimethyl, 3,4-dimethyl, 2,5-dimethyl, 4-nitro, 2,6-dinitro-4-trifluormethyl and 5-chloro-2-methyl-aminophenyl.

Examples of substituted pyrrolidino radicals which may be mentioned are the 2-methoxymethylpyrrolidino, 2-methoxycarbonylpyrrolidino, 2-methylpyrrolidino, 2,5-dimethylpyrrolidino, 2-carboxypyrrolidino, 4-hydroxy-2-methoxycarbonylpyrrolidino, 4-hydroxy-2-ethoxycarbonylpyrrolidino, 2-(2-hydroxyethyl)pyrrolidino, 4-hydroxy-2-carboxypyrrolidino, 2-hydroxymethylpyrrolidino, 3-hydroxy-pyrrolidino and the 4-acetoxy-2-carboxypyrrolidino radicals.

Examples of substituted piperidino radicals which may be mentioned are the 2-carboxypiperidino, 2-n-propylpiperidino, 5-ethyl-2-methylpiperidino, 4-hydroxymethyl-4-phenylpiperidino, 4-n-propylpiperidino, 4-(3-phenylpropyl)piperidino, 2,6-dimethylpiperidino, 4-phenyl-4-propyloxycarbonylpiperidino, 4-ethoxycarbonyl-4-phenylpiperidino, 4-carboxy4-phenylpiperidino, 4-carboxypiperidino, 4-(4-fluorobenzoyl)piperidino, 4-(4-chlorobenzoyl)piperidino, 2,3-dicarboxypiperidino, 2,4-dicarboxypiperidino, 2,6-dicarboxypiperidino, 2-ethoxycarbonylpiperidino, 2-methylpiperidino, 2,6-dimethylpiperidino, 2-hydroxymethylpiperidino, 2-ethylpiperidino, 2-(2-hydroxyethyl)piperidino, 3-ethoxycarbonylpiperidino and the 4-benzylpiperidino radicals.

Examples of substituted piperazino radicals which may be mentioned are the 4-methylpiperazino, 4-phenylpiperazino, 4-(2-methylphenyl)piperazino, 4-(2,3-dimethylphenyl)piperazino, 4-(2-chlorophenyl)piperazino, 4-(2-methoxyphenyl)piperazino, 4-(2-ethoxyphenyl)piperazino, 4-(3-chlorophenyl)piperazino, 4-(4-fluorophenyl)piperazino, 4-(4-chlorophenyl)piperazino, 4-(4-methoxyphenyl)piperazino, 4-carbamoylpiperazino, 3-methyl-4-(4-chlorophenyl)piperazino, 3-methyl4-(4-methoxyphenyl)piperazino, 3-methyl-4-(4-methylphenyl)piperazino, 4-(2,4-dimethylphenyl)piperazino, 4-(3,4-dichlorophenyl)piperazino, 4-(3,4-dimethylphenyl)piperazino, 3-methyl4-(2,5di-phenylpiperazino, 3-methyl4-(3-chlorophenyl)piperazino, 4-benzylpiperazino, 4-propylpiperazino, 4-(3-methylphenyl)piperazino, 4-(3-methoxyphenyl)piperazino, 4-(4-methylphenyl)piperazino, 4-(2,5-di-methylphenyl)piperazino, 4-cyclopropylpiperazino, 4-cyclobutylpiperazino, 4-cyclopentylpiperazino, 4-cyclohexylpiperazino, 4-cycloheptylpiperazino, 4-n-butylpiperazino, 4-isobutylpiperazino, 4-tert-butylpiperazino, 4-(1-phenylethyl)piperazino, 4-ethoxycarbonylmethylpiperazino, 4-(2-phenylethyl)piperazino, 4-(2-cyclohexylethyl)piperazino, 4-(2-hydroxyphenyl)piperazino, 4-(3,4-dimethoxyphenyl)piperazino, 4-isopropylpiperazino, 3-methyl4-(3-methoxyphenyl)piperazino, 4-(4-hydroxyphenyl)piperazino, 3-methyl4-(3-methylphenyl)piperazino, 4-(3-hydroxyphenyl)piperazino, 4-(2,6-di-nitro-4-trifluoromethylphenyl)piperazino, 4-(4-nitrophenyl)piperazino, 4-(4-acetylphenyl)piperazino, 4-(2-chloro-5-thienylmethyl)piperazino and the 4-[2-(2-methyl-5-nitro-1-imidazolyl)ethyl]piperazino radicals.

An example of a substituted morpholino radical which may be mentioned is the 3,5-dimethylmorpholino radical.

An example of a substituted thiomorpholino radical which may be mentioned is the 2-carboxythiomorpholino radical.

Examples of substituted indolin-1-yl radicals which may be mentioned are the 2-carboxy-1-indolinyl, 6-fluoro-1-indolinyl, 5-bromo-1-indolinyl, 2,7-dimethyl-l-indolinyl, 2-methyl-1-indolinyl, 5-bromo-7-nitro-1-indolinyl, 5-nitro-1 -indolinyl, 2,3-dimethyl-1 -indolinyl and the 6-nitro-1 -indolinyl radicals.

Examples of substituted 1,2,3,4-tetrahydroquinoline radicals which may be mentioned are the 2-ethoxycarbonyl-1,2,3,4-tetrahydro-1-quinolinyl, 2-methyl-1,2,3,4-tetrahydro-1-quinolinyl, 6-methyl-1,2,3,4-tetrahydro-1-quinolinyl, 6-fluoro-2-methyl-1,2,3,4-tetrahydro-1-quinolinyl, 4-methyl-1,2,3,4-tetrahydro-1-quinolinyl and the 2-fluoro-6-methyl-1,2,3,4-tetrahydro-1-quinolinyl radicals.

An example of a substituted 1,2,3,4-tetrahydroisoquinoline radical which may be mentioned is the 3-carboxy-1,2,3,4-tetrahydro-2-isoquinolinyl radical.

Exemplary quinolin-3-yl radicals—with the substituents R1, R2 and R3 in the positions 2, 4, 5, 6, 7 or 8-which may be mentioned with the aid of the "Table of quinolin-3-yl radicals" are the following radicals:

Table of quinolin-3-yl radicals

| positions of the substituents | 2 | 4 | 5 | 6 | 7 | 8 |
|---|---|---|---|---|---|---|
| | H | H | H | H | H | H |
| | Me | H | H | H | H | H |
| | H | H | H | Me | H | H |
| | H | Me | H | H | H | H |
| | H | H | H | H | Cl | H |
| | OH | H | H | H | H | H |
| | Cl | H | H | H | H | H |
| | OMe | H | H | H | H | H |
| | OEt | H | H | H | H | H |
| | Me | Cl | H | H | H | H |
| | Me | OH | H | H | H | H |
| | H | OH | H | H | Me | H |
| | H | Me | H | Cl | H | H |
| | H | Me | H | H | Cl | H |
| | H | OMe | H | H | H | H |
| | H | Me | H | Me | Me | H |
| | H | OH | H | Cl | H | H |
| | H | OH | H | OH | H | H |
| | OH | OH | H | H | H | H |
| | H | Cl | H | H | Cl | H |
| | H | OH | H | H | Cl | H |
| | OH | Me | H | Me | H | H |
| | H | OH | H | OMe | H | H |
| | Me | OMe | H | H | H | H |
| | H | OEt | H | H | H | H |
| | Me | H | H | OMe | OMe | H |
| | H | Cl | Cl | H | H | H |
| | H | COOH | H | H | H | H |
| | Me | COOH | H | H | H | H |
| | H | COOH | H | Cl | H | H |
| | H | OH | H | OMe | H | OMe |
| | H | OH | H | H | COOH | H |
| | H | Br | H | H | H | H |
| | SMe | Me | H | H | H | H |
| | H | Me | H | OMe | H | H |
| | COOH | Me | H | H | H | H |
| | COOH | OH | H | H | H | H |
| | COOH | Cl | H | H | H | H |
| | Br | H | H | H | H | H |
| | H | H | H | OMe | H | H |
| | H | H | H | H | H | OMe |
| | H | H | H | H | H | OH |
| | H | H | H | OMe | OMe | H |
| | H | SEt | H | H | H | H |
| | H | OMe | H | H | Cl | H |
| | Me | OH | H | H | H | Me |

In the above table, Me is $CH_3$ and Et is $C_2H_5$.

Suitable salts of compounds of the formula I—depending on substitution—are all acid addition salts or all salts with bases. Particular mention may be made of the pharmacologically tolerable salts of the inorganic and organic acids and bases customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids can be employed in salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

It is known to the person skilled in the art that the compounds according to the invention, as well as their salts, if they are isolated, for example, in crystalline form, can contain various amounts of solvents. The invention therefore also includes all solvates and in particular all hydrates of the compounds of the formula I, and all solvates and in particular all hydrates of the salts of the compounds of the formula I.

One embodiment (embodiment a) of the invention relates to compounds of the formula I in which A is 2–7C-alkylene, X is O (oxygen) and Y is S, t is the number 1 and u is the number 0.

A further embodiment (embodiment b) of the invention relates to compounds of the formula I in which A is 2–7C-alkylene, X is S and Y is S, t is the number 1 and u is the number 0.

A further embodiment (embodiment c) of the invention relates to compounds of the formula I in which A is 2–7C-alkylene, X is S and Y is 1,4-piperazinylene, t is the number 1 and u is the number 0.

A further embodiment (embodiment d) of the invention relates to compounds of the formula I in which A is 1–7C-alkylene, X is S and t and u are the number 0.

A further embodiment (embodiment e) of the invention relates to compounds of the formula I in which A is 2–7C-alkylene, X is S and Z is S, n and t are the number 0 and u is the number 1.

A further embodiment (embodiment f) of the invention relates to compounds of the formula I in which A is 2–7C-alkylene, X is S and Y is 1,4-piperazinylene, t is the number 1 and u is the number 0 and G is the part of the compound of the formula I bonded to A (including S and via S).

A further embodiment (embodiment g) of the invention relates to compounds of the formula I in which A is 1–7C-alkylene, X is O (oxygen) and t and u are the number 0.

A further embodiment (embodiment h) of the invention relates to compounds of the formula I in which A is 2–7C-alkylene, X is O (oxygen) and Y is 1,4-piperazinyl, t is the number 1 and u is the number 0.

A further embodiment (embodiment i) of the invention relates to compounds of the formula I in which A is 2–7C-alkylene, X is S and Z is NH, n and t are the number 0 and u is the number 1.

A further embodiment (embodiment j) of the invention relates to compounds of the formula I in which A is 2–7C-alkylene, X is O (oxygen) and Z is S, n and t are the number 0 and u is the number 1.

A further embodiment (embodiment k) of the invention relates to compounds of the formula I in which A is 1–7C-alkylene, 2–7C-alkenylene, 3–7C-cycloalkylene or phenylene, t and u are the number 0 and G is hydrogen.

A further embodiment (embodiment l) of the invention relates to compounds of the formula I in which A is 2–7C-alkylene, X is N-1–4C-alkyl and Y is S, t is the number 1 and u is the number 0.

A further embodiment (embodiment m) of the invention relates to compounds of the formula I in which A is 2–7C-alkylene, X is S, Y is O (oxygen) and Z is O (oxygen), t and u are the number 1, m is a number from 2 to 7, n is the number 0 and G is 1–4C-alkyl which is completely or mainly substituted by fluorine.

A further embodiment (embodiment n) of the invention relates to compounds of the formula I in which A is 2–7C-alkylene, X is N-1–4C-alkyl and Z is O (oxygen), t and n are the number 0 and u is the number 1.

A further embodiment (embodiment o) of the invention relates to compounds of the formula I in which A is 2–7C-alkylene, X is N-1–4C-alkyl and Z is S, t and n are the number 0 and u is the number 1.

A further embodiment (embodiment p) of the invention relates to compounds of the formula I in which A is 2–7C-alkylene, X is S and Z is O (oxygen), t and n are the number 0 and u is the number 1.

A further embodiment (embodiment q) of the invention relates to compounds of the formula I in which A is 2–7C-alkylene, X is N-1–4C-alkyl and Z is O (oxygen), t and n are the number 0 and u is the number 1 and G is hydrogen.

A further embodiment (embodiment r) of the invention relates to compounds of the formula I in which A is 2–7C-alkylene, X is N-1–4C-alkyl and t and u are the number 0.

A further embodiment (embodiment s) of the invention relates to compounds of the formula I in which A is 2–7C-alkylene, X is S, Y is S, Z is O (oxygen) and t and u are the number 1.

A further embodiment (embodiment t) of the invention relates to compounds of the formula I in which A is 2–7C-alkylene, X is O (oxygen), Y is S, Z is O (oxygen) and t and u are the number 1.

A further embodiment (embodiment u) of the invention relates to compounds of the formula I in which A is 2–7C-alkylene, X is O (oxygen), Y is O (oxygen), Z is S and t and u are the number 1.

Compounds of the embodiments I, n, o, q and r which are particularly worthy of mention are those in which R7 is halogen, in particular chlorine.

Compounds of the embodiments e, i, j, n, o and p which are particularly worthy of mention are those in which G is 3-nitroimidazo[1,2-b]pyridazin-6-yl.

Preferred compounds of the invention are those of the embodiments c, d, e, f, j, m, s, t and u.

Particularly preferred compounds of the invention are those of the embodiments a and b.

One group of compounds according to the invention are those compounds, in which G has the meaning oxazolidinone and/or R17 has the meaning 3–7C-cycloalkyl or pyridinyl.

Another group of compounds according to the invention are those compounds, in which the meaning of G is other than oxazolidinone and the meaning of R17 is other than 3–7C-cycloalkyl and pyridinyl.

Compounds according to the invention to be emphasized are those of the formula I in which R1, R2 and R3 are identical to or different from one another and are hydrogen or halogen, R4 is hydrogen, R5 is hydrogen, R6 is hydrogen, R7 is hydrogen, 1–4C-alkyl or halogen, R8 is hydrogen, R9 is hydrogen, A is 1–7C-alkylene, G is hydrogen, 1–4C-alkyl which is completely or mainly substituted by fluorine, the radical —N(R10)R11, the part of the compound of the above formula I bonded to A (including X and via X) or a cyclic system or bicyclic system which is unsubstituted or substituted by R12 and R13 and which is selected from the group consisting of benzene, naphthalene, furan, thiophene, pyrrole, oxazole, oxazoline, oxazolidinone, isoxazole, thiazole, thiazoline, isothiazole, imidazole, imidazoline, pyrazole, triazole, tetrazole, thiadiazole, thiadiazole 1-oxide, oxadiazole, pyridine, pyridine N-oxide, pyrimidine, chloropyrimidine, piperidine, triazine, pyridone, benzimidazole, imidazopyridine, benzothiazole, benzoxazole, quinoline and imidazopyridazine, in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino radical is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino radical can be substituted in the 2-, 3-, 5- or 6-position by a 1–4C-alkyl radical, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl, a substituted morpholino radical is substituted by one or two identical or different 1–4C-alkyl radicals, a substituted thiomorpholino radical is substituted by one or two identical or different 1–4C-alkyl radicals or a carboxyl group, a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C-alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 3–7C-cycloalkyl, 1–4C-alkoxy, carboxyl, 1–4C-alkoxycarbonyl, pyridinyl or —N(R18)R19, where R18 is hydrogen, 1–4C-alkyl or —CO—R20 and R19 is hydrogen or 1–4C-alkyl, or where R18 and R19, together and including the nitrogen atom to which both are bonded, are a piperidino or morpholino radical, R20 is hydrogen, 1–4C-alkyl or 1–4C-alkoxy, X is O (oxygen), N-1–4C-alkyl, NH or S, Y is O (oxygen), N-1–4C-alkyl, NH, S or 1,4-piperazinylene, Z is O (oxygen), N-1–4C-alkyl, NH or S, m is a number from 1 to 7, n is a number from 0 to 4, t is the number 0 or 1 and u is the number 0 or 1, and their salts.

Compounds according to the invention to be emphasized particularly are those of the formula I in which R1, R2 and R3 are hydrogen, R4 is hydrogen, R5 is hydrogen, R6 is hydrogen, R7 is 1–4C-alkyl or halogen, R8 is hydrogen, R9 is hydrogen, A is 1–7C-alkylene, G is hydrogen, 1–4C-alkyl which is completely or mainly substituted by fluorine, the radical —N(R10)R11 or a cyclic system which is unsubstituted or substituted by R12 and R13 and which is selected from the group consisting of benzene, furan, thiophene, oxazole, oxazoline, oxazolidinone, thiazole, imidazole, triazole, tetrazole, pyridine, pyrimidine, chloropyrimidine, piperidine and imidazopyridazine, in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, 1,2,3,4-tetrahydroquinoline and 1,2,3,4-tetrahydroisoquinoline, where a substituted piperazino radical is substituted in the 4-position by a substituent selected from the group consisting of 1–4C-alkyl and carbamoyl, R12 is hydrogen, 1–4C-alkyl, hydroxyl, halogen, nitro, carboxyl, 1–4C-alkoxycarbonyl or 1–4C-alkyl substituted by R17, R13 is hydrogen or 1–4C-alkyl, R17 is 3–7C-cycloalkyl or pyridinyl, X is O (oxygen), N-1–4C-alkyl or S, Y is O (oxygen), S or 1,4-piperazinylene, Z is O (oxygen) or S, m is a number from 1 to 4, n is a number from 0 to 2, t is the number 0 or 1 and u is the number 0 or 1, and their salts.

Preferred compounds according to the invention are those of the formula I in which R1, R2 and R3 are hydrogen, R4 is hydrogen, R5 is hydrogen, R6 is hydrogen, R7 is 1–4C-alkyl R8 is hydrogen, R9 is hydrogen, A is 2–4C-alkylene, G is hydrogen, 1–4C-alkyl which is completely or mainly substituted by fluorine or a cyclic system which is unsubstituted or substituted by R12 and R13 and which is selected from the group consisting of thiophene, oxazoline, oxazolidinone, imidazole, pyridine, pyrimidine and piperidine in which R12 is hydrogen, 1–4C-alkyl, hydroxyl, halogen, nitro or 1–4C-alkyl substituted by R17, R13 is hydrogen or 1–4C-alkyl, R17 is 3–7C-cycloalkyl or pyridinyl, X is O (oxygen) or S, Y is O (oxygen), S or 1,4-piperazinylene, Z is O (oxygen) or S, m is a number from 1 to 3, n is the number 0 or 1, t is the number 0 or 1 and u is the number 0 or 1, and their salts.

Preferred embodiments of the invention are those of embodiments a to u, in which the substituents and symbols have the meanings of the preferred compounds according to the invention.

Exemplary compounds according to the invention are listed in the following tables:

TABLE 1

Compounds of the formula I in embodiment a (see above) with R1, R2, R3, R4, R5, R6, R8 and R9 = H, R7 = CH₃ and the following further substituent and symbol meanings:

| A | m | G |
| --- | --- | --- |
| —(CH₂)₂— | 2 | 2-Methyl-5-nitroimidazol-1-yl |
| —(CH₂)₂— | 3 | 2-Methyl-5-nitroimidazol-1-yl |
| —(CH₂)₂— | 4 | 2-Methyl-5-nitroimidazol-1-yl |
| —(CH₂)₃— | 2 | 2-Methyl-5-nitroimidazol-1-yl |
| —(CH₂)₃— | 3 | 2-Methyl-5-nitroimidazol-1-yl |
| —(CH₂)₃— | 4 | 2-Methyl-5-nitroimidazol-1-yl |
| —(CH₂)₄— | 2 | 2-Methyl-5-nitroimidazol-1-yl |
| —(CH₂)₄— | 3 | 2-Methyl-5-nitroimidazol-1-yl |
| —(CH₂)₄— | 4 | 2-Methyl-5-nitroimidazol-1-yl |
| —(CH₂)₅— | 2 | 2-Methyl-5-nitroimidazol-1-yl |
| —(CH₂)₅— | 3 | 2-Methyl-5-nitroimidazol-1-yl |
| —(CH₂)₆— | 2 | 2-Methyl-5-nitroimidazol-1-yl |
| —(CH₂)₂— | 1 | 4-Pyridinyl |
| —(CH₂)₂— | 2 | 4-Pyridinyl |
| —(CH₂)₂— | 3 | 4-Pyridinyl |

TABLE 1-continued

Compounds of the formula I in embodiment a (see above) with R1, R2, R3, R4, R5, R6, R8 and R9 = H, R7 = CH₃ and the following further substituent and symbol meanings:

| A | m | G |
| --- | --- | --- |
| —(CH₂)₂— | 4 | 4-Pyridinyl |
| —(CH₂)₃— | 1 | 4-Pyridinyl |
| —(CH₂)₃— | 2 | 4-Pyridinyl |
| —(CH₂)₃— | 3 | 4-Pyridinyl |
| —(CH₂)₃— | 4 | 4-Pyridinyl |
| —(CH₂)₄— | 1 | 4-Pyridinyl |
| —(CH₂)₄— | 2 | 4-Pyridinyl |
| —(CH₂)₄— | 3 | 4-Pyridinyl |
| —(CH₂)₄— | 4 | 4-Pyridinyl |
| —(CH₂)₅— | 1 | 4-Pyridinyl |
| —(CH₂)₅— | 2 | 4-Pyridinyl |
| —(CH₂)₅— | 3 | 4-Pyridinyl |
| —(CH₂)₆— | 1 | 4-Pyridinyl |
| —(CH₂)₆— | 2 | 4-Pyridinyl |
| —(CH₂)₂— | 1 | 2-Pyrimidinyl |
| —(CH₂)₂— | 2 | 2-Pyrimidinyl |
| —(CH₂)₂— | 3 | 2-Pyrimidinyl |
| —(CH₂)₂— | 4 | 2-Pyrimidinyl |
| —(CH₂)₃— | 1 | 2-Pyrimidinyl |
| —(CH₂)₃— | 2 | 2-Pyrimidinyl |
| —(CH₂)₃— | 3 | 2-Pyrimidinyl |
| —(CH₂)₃— | 4 | 2-Pyrimidinyl |
| —(CH₂)₄— | 1 | 2-Pyrimidinyl |
| —(CH₂)₄— | 2 | 2-Pyrimidinyl |
| —(CH₂)₄— | 3 | 2-Pyrimidinyl |
| —(CH₂)₄— | 4 | 2-Pyrimidinyl |
| —(CH₂)₅— | 1 | 2-Pyrimidinyl |
| —(CH₂)₅— | 2 | 2-Pyrimidinyl |
| —(CH₂)₅— | 3 | 2-Pyrimidinyl |
| —(CH₂)₆— | 1 | 2-Pyrimidinyl |
| —(CH₂)₆— | 2 | 2-Pyrimidinyl |

TABLE 2

Compounds of the formula I in embodiment b (see above) with R1, R2, R3, R4, R5, R6, R8 and R9 = H, R7 = CH₃ and the further substituent and symbol meanings for A, m and G as indicated in Table 1.

TABLE 3

Compounds of the formula I in embodiment c (see above) with R1, R2, R3, R4, R5, R6, R8 and R9 = H, R7 = CH₃ and the further substituent and symbol meanings for A, m and G as indicated in Table 1.

TABLE 4

Compounds of the formula I in embodiment h (see above) with R1, R2, R3, R4, R5, R6, R8 and R9 = H, R7 = CH₃ and the further substituent and symbol meanings for A, m and G as indicated in Table 1.

TABLE 5

Compounds of the formula I in embodiment I (see above) with R1, R2, R3, R4, R5, R6, R8 and R9 = H, R7 = CH₃ and the further substituent and symbol meanings for A, m and G as indicated in Table 1.

TABLE 6

Compounds of the formula I in embodiment d (see above) with R1, R2, R3, R4, R5, R6, R8 and R9 = H, R7 = CH$_3$ and the following further substituent and symbol meanings:

| A | G |
|---|---|
| —(CH$_2$)$_2$— | 2-Methyl-5-nitroimidazol-1-yl |
| —(CH$_2$)$_3$— | 2-Methyl-5-nitroimidazol-1-yl |
| —(CH$_2$)$_4$— | 2-Methyl-5-nitroimidazol-1-yl |
| —(CH$_2$)$_5$— | 2-Methyl-5-nitroimidazol-1-yl |
| —(CH$_2$)$_6$— | 2-Methyl-5-nitroimidazol-1-yl |
| —CH$_2$— | 4-Pyridinyl |
| —(CH$_2$)$_2$— | 4-Pyridinyl |
| —(CH$_2$)$_3$— | 4-Pyridinyl |
| —(CH$_2$)$_4$— | 4-Pyridinyl |
| —(CH$_2$)$_5$— | 4-Pyridinyl |
| —(CH$_2$)$_6$— | 4-Pyridinyl |
| —CH$_2$— | 2-Pyrimidinyl |
| —(CH$_2$)$_2$— | 2-Pyrimidinyl |
| —(CH$_2$)$_3$— | 2-Pyrimidinyl |
| —(CH$_2$)$_4$— | 2-Pyrimidinyl |
| —(CH$_2$)$_5$— | 2-Pyrimidinyl |
| —(CH$_2$)$_6$— | 2-Pyrimidinyl |

TABLE 7

Compounds of the formula I in embodiment g (see above) with R1, R2, R3, R4, R5, R6, R8 and R9 = H, R7 = CH$_3$ and the further substituent and symbol meanings for A and G as indicated n Table 6.

TABLE 8

Compounds of the formula I in embodiment e (see above) with R1, R2, R3, R4, R5, R6, R8 and R9 = H, R7 = CH$_3$ and the following further substituent and symbol meanings:

| A | G |
|---|---|
| —(CH$_2$)$_2$— | 4-Pyridinyl |
| —(CH$_2$)$_3$— | 4-Pyridinyl |
| —(CH$_2$)$_4$— | 4-Pyridinyl |
| —(CH$_2$)$_5$— | 4-Pyridinyl |
| —(CH$_2$)$_6$— | 4-Pyridinyl |
| —(CH$_2$)$_2$— | 2-Pyrimidinyl |
| —(CH$_2$)$_3$— | 2-Pyrimidinyl |
| —(CH$_2$)$_4$— | 2-Pyrimidinyl |
| —(CH$_2$)$_5$— | 2-Pyrimidinyl |
| —(CH$_2$)$_6$— | 2-Pyrimidinyl |
| —(CH$_2$)$_2$— | 3-Nitroimidazo[1,2-b]pyridazin-6-yl |
| —(CH$_2$)$_3$— | 3-Nitroimidazo[1,2-b]pyridazin-6-yl |
| —(CH$_2$)$_4$— | 3-Nitroimidazo[1,2-b]pyridazin-6-yl |
| —(CH$_2$)$_5$— | 3-Nitroimidazo[1,2-b]pyridazin-6-yl |
| —(CH$_2$)$_6$— | 3-Nitroimidazo[1,2-b]pyridazin-6-yl |

TABLE 9

Compounds of the formula I in embodiment i (see above) with R1, R2, R3, R4, R5, R6, R8 and R9 = H, R7 = CH$_3$ and the further substituent and symbol meanings for A and G as indicated in Table 8.

TABLE 10

Compounds of the formula I in embodiment j (see above) with R1, R2, R3, R4, R5, R6, R8 and R9 = H, R7 = CH$_3$ and the further substituent and symbol meanings for A and G as indicated in Table 8.

TABLE 11

Compounds of the formula I in embodiment n (see above) with R1, R2, R3, R4, R5, R6, R8 and R9 = H, R7 = Cl and the further substituent and symbol meanings for A and G as indicated in Table 8.

TABLE 12

Compounds of the formula I in embodiment o (see above) with R1, R2, R3, R4, R5, R6, R8 and R9 = H, R7 = Cl and the further substituent and symbol meanings for A and G as indicated in Table 8.

TABLE 13

Compounds of the formula I in embodiment p (see above) with R1, R2, R3, R4, R5, R6, R8 and R9 = H, R7 = CH$_3$ and the further substituent and symbol meanings for A and G as indicated in Table 8.

TABLE 14

Compounds of the formula I in embodiment m (see above) with R1, R2, R3, R4, R5, R6, R8 and R9 = H, R7 = CH$_3$ and the following further substituent and symbol meanings:

| A | m | G |
|---|---|---|
| —(CH$_2$)$_2$— | 2 | 2,2,2-Trifluoroethyl |
| —(CH$_2$)$_2$— | 3 | 2,2,2-Trifluoroethyl |
| —(CH$_2$)$_2$— | 4 | 2,2,2-Trifluoroethyl |
| —(CH$_2$)$_3$— | 2 | 2,2,2-Trifluoroethyl |
| —(CH$_2$)$_3$— | 3 | 2,2,2-Trifluoroethyl |
| —(CH$_2$)$_3$— | 4 | 2,2,2-Trifluoroethyl |
| —(CH$_2$)$_4$— | 2 | 2,2,2-Trifluoroethyl |
| —(CH$_2$)$_4$— | 3 | 2,2,2-Trifluoroethyl |
| —(CH$_2$)$_4$— | 4 | 2,2,2-Trifluoroethyl |
| —(CH$_2$)$_5$— | 1 | 2,2,2-Trifluoroethyl |
| —(CH$_2$)$_5$— | 2 | 2,2,2-Trifluoroethyl |
| —(CH$_2$)$_5$— | 3 | 2,2,2-Trifluoroethyl |
| —(CH$_2$)$_6$— | 1 | 2,2,2-Trifluoroethyl |
| —(CH$_2$)$_6$— | 2 | 2,2,2-Trifluoroethyl |
| —(CH$_2$)$_2$— | 2 | Trifluoromethyl |
| —(CH$_2$)$_2$— | 3 | Trifluoromethyl |
| —(CH$_2$)$_2$— | 4 | Trifluoromethyl |
| —(CH$_2$)$_3$— | 2 | Trifluoromethyl |
| —(CH$_2$)$_3$— | 3 | Trifluoromethyl |
| —(CH$_2$)$_3$— | 4 | Trifluoromethyl |
| —(CH$_2$)$_4$— | 2 | Trifluoromethyl |
| —(CH$_2$)$_4$— | 3 | Trifluoromethyl |
| —(CH$_2$)$_4$— | 4 | Trifluoromethyl |
| —(CH$_2$)$_5$— | 2 | Trifluoromethyl |
| —(CH$_2$)$_5$— | 3 | Trifluoromethyl |
| —(CH$_2$)$_6$— | 2 | Trifluoromethyl |
| —(CH$_2$)$_2$— | 2 | Difluoromethyl |
| —(CH$_2$)$_2$— | 3 | Difluoromethyl |
| —(CH$_2$)$_2$— | 4 | Difluoromethyl |
| —(CH$_2$)$_3$— | 2 | Difluoromethyl |
| —(CH$_2$)$_3$— | 3 | Difluoromethyl |
| —(CH$_2$)$_3$— | 4 | Difluoromethyl |
| —(CH$_2$)$_4$— | 2 | Difluoromethyl |
| —(CH$_2$)$_4$— | 3 | Difluoromethyl |
| —(CH$_2$)$_4$— | 4 | Difluoromethyl |
| —(CH$_2$)$_5$— | 2 | Difluoromethyl |
| —(CH$_2$)$_5$— | 3 | Difluoromethyl |
| —(CH$_2$)$_6$— | 2 | Difluoromethyl |

TABLE 15

Compounds of the formula I in embodiment q (see above) with R1, R2, R3, R4, R5, R6, R8 and R9 = H and the following further substituent and symbol meanings:

| A | R7 |
|---|---|
| —(CH$_2$)$_2$— | CH$_3$ |
| —(CH$_2$)$_3$— | CH$_3$ |
| —(CH$_2$)$_4$— | CH$_3$ |
| —(CH$_2$)$_5$— | CH$_3$ |
| —(CH$_2$)$_6$— | CH$_3$ |
| —(CH$_2$)$_2$— | Cl |
| —(CH$_2$)$_3$— | Cl |
| —(CH$_2$)$_4$— | Cl |
| —(CH$_2$)$_5$— | Cl |
| —(CH$_2$)$_6$— | Cl |

TABLE 16

Compounds of the formula I in embodiment r (see above) with R1, R2, R3, R4, R5, R6, R8 and R9 = H and the following further substituent and symbol meanings:

| A | R7 | G |
|---|---|---|
| —(CH$_2$)$_2$— | CH$_3$ | 1,2,3,4-Tetrahydroisoquinolin-2-yl |
| —(CH$_2$)$_3$— | CH$_3$ | 1,2,3,4-Tetrahydroisoquinolin-2-yl |
| —(CH$_2$)$_4$— | CH$_3$ | 1,2,3,4-Tetrahydroisoquinolin-2-yl |
| —(CH$_2$)$_5$— | CH$_3$ | 1,2,3,4-Tetrahydroisoquinolin-2-yl |
| —(CH$_2$)$_6$— | CH$_3$ | 1,2,3,4-Tetrahydroisoquinolin-2-yl |
| —(CH$_2$)$_2$— | Cl | 1,2,3,4-Tetrahydroisoquinolin-2-yl |
| —(CH$_2$)$_3$— | Cl | 1,2,3,4-Tetrahydroisoquinolin-2-yl |
| —(CH$_2$)$_4$— | Cl | 1,2,3,4-Tetrahydroisoquinolin-2-yl |
| —(CH$_2$)$_5$— | Cl | 1,2,3,4-Tetrahydroisoquinolin-2-yl |
| —(CH$_2$)$_6$— | Cl | 1,2,3,4-Tetrahydroisoquinolin-2-yl |
| —(CH$_2$)$_2$— | CH$_3$ | 6,7-Dimethoxy-1,2,3,4-tetrahydroisoquinolin-2-yl |
| —(CH$_2$)$_3$— | CH$_3$ | 6,7-Dimethoxy-1,2,3,4-tetrahydroisoquinolin-2-yl |
| —(CH$_2$)$_4$— | CH$_3$ | 6,7-Dimethoxy-1,2,3,4-tetrahydroisoquinolin-2-yl |
| —(CH$_2$)$_5$— | CH$_3$ | 6,7-Dimethoxy-1,2,3,4-tetrahydroisoquinolin-2-yl |
| —(CH$_2$)$_6$— | CH$_3$ | 6,7-Dimethoxy-1,2,3,4-tetrahydroisoquinolin-2-yl |
| —(CH$_2$)$_2$— | Cl | 6,7-Dimethoxy-1,2,3,4-tetrahydroisoquinolin-2-yl |
| —(CH$_2$)$_3$— | Cl | 6,7-Dimethoxy-1,2,3,4-tetrahydroisoquinolin-2-yl |
| —(CH$_2$)$_4$— | Cl | 6,7-Dimethoxy-1,2,3,4-tetrahydroisoquinolin-2-yl |
| —(CH$_2$)$_5$— | Cl | 6,7-Dimethoxy-1,2,3,4-tetrahydroisoquinolin-2-yl |
| —(CH$_2$)$_6$— | Cl | 6,7-Dimethoxy-1,2,3,4-tetrahydroisoquinolin-2-yl |

TABLE 17

Compounds of the formula I in embodiment s (see above) with R1, R2, R3, R4, R5, R6, R8 and R9 = H, R7 = CH$_3$, n = 1 and the following further substituent and symbol meanings:

| A | m | G |
|---|---|---|
| —(CH$_2$)$_2$— | 1 | 4-Pyridinyl |
| —(CH$_2$)$_2$— | 2 | 4-Pyridinyl |
| —(CH$_2$)$_2$— | 3 | 4-Pyridinyl |
| —(CH$_2$)$_2$— | 4 | 4-Pyridinyl |
| —(CH$_2$)$_3$— | 1 | 4-Pyridinyl |
| —(CH$_2$)$_3$— | 2 | 4-Pyridinyl |
| —(CH$_2$)$_3$— | 3 | 4-Pyridinyl |
| —(CH$_2$)$_3$— | 4 | 4-Pyridinyl |
| —(CH$_2$)$_4$— | 1 | 4-Pyridinyl |
| —(CH$_2$)$_4$— | 2 | 4-Pyridinyl |
| —(CH$_2$)$_4$— | 3 | 4-Pyridinyl |
| —(CH$_2$)$_4$— | 4 | 4-Pyridinyl |
| —(CH$_2$)$_5$— | 1 | 4-Pyridinyl |
| —(CH$_2$)$_5$— | 2 | 4-Pyridinyl |
| —(CH$_2$)$_5$— | 3 | 4-Pyridinyl |
| —(CH$_2$)$_6$— | 1 | 4-Pyridinyl |
| —(CH$_2$)$_6$— | 2 | 4-Pyridinyl |
| —(CH$_2$)$_2$— | 1 | 2-Pyrimidinyl |
| —(CH$_2$)$_2$— | 2 | 2-Pyrimidinyl |
| —(CH$_2$)$_2$— | 3 | 2-Pyrimidinyl |
| —(CH$_2$)$_2$— | 4 | 2-Pyrimidinyl |
| —(CH$_2$)$_3$— | 1 | 2-Pyrimidinyl |
| —(CH$_2$)$_3$— | 2 | 2-Pyrimidinyl |
| —(CH$_2$)$_3$— | 3 | 2-Pyrimidinyl |
| —(CH$_2$)$_3$— | 4 | 2-Pyrimidinyl |
| —(CH$_2$)$_4$— | 1 | 2-Pyrimidinyl |
| —(CH$_2$)$_4$— | 2 | 2-Pyrimidinyl |
| —(CH$_2$)$_4$— | 3 | 2-Pyrimidinyl |
| —(CH$_2$)$_4$— | 4 | 2-Pyrimidinyl |
| —(CH$_2$)$_5$— | 1 | 2-Pyrimidinyl |
| —(CH$_2$)$_5$— | 2 | 2-Pyrimidinyl |
| —(CH$_2$)$_5$— | 3 | 2-Pyrimidinyl |
| —(CH$_2$)$_6$— | 1 | 2-Pyrimidinyl |
| —(CH$_2$)$_6$— | 2 | 2-Pyrimidinyl |

TABLE 18

Compounds of the formula I in embodiment t (see above) with R1, R2, R3, R4, R5, R6, R8 and R9 = H, R7 = CH$_3$, n = 1 and the further substituent and symbol meanings for A, m and G as indicated in Table 17

TABLE 19

Compounds of the formula I in embodiment u (see above) with R1, R2, R3, R4, R5, R6, R8 and R9 = H, R7 = CH$_3$, n = 1 and the further substituent and symbol meanings for A, m and G as indicated in Table 17 and the salts of the compounds mentioned in Tables 1 to 19.

The compounds of the formula I according to the invention can be prepared in various ways. In principle, the compounds of the formula I can be prepared by reaction of the aminoquinolines of the formula II with the 2-halomethylpyridines of the formula III (Hal = halogen, in particular chlorine) in a manner known per se.

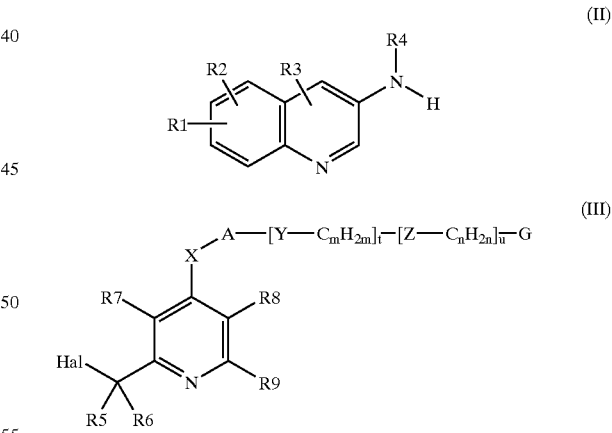

If appropriate, it may be useful to introduce the radical —X—A—[Y—C$_m$H$_{2m}$]$_t$—[Z—C$_n$H$_{2n}$]$_u$—G completely or partially into the 4-position of the pyridine only after the reaction of an appropriately substituted 2-halomethylpyridine with the aminoquinoline II. The manner in which the compounds according to the invention can be obtained is shown in exemplary form in the following examples.

The compounds of the formula 11 are known or can be prepared in a known manner analogously to known compounds.

The compounds of the formula III are also known (see, for example, the abovementioned International Patent Applications in the section "Known Technical Background") or the abovementioned complete or partial introduction of the radical —X—A—[Y—C$_m$H$_{2m}$]$_t$—[Z—C$_n$H$_{2n}$]—G is described in the International Patent Applications mentioned.

The following examples explain the invention in greater detail without restricting it. The exemplary final products and the salts of these compounds are preferred subject matter of the invention. The compounds according to the invention and the starting compounds can be prepared in a manner analogous to that described in the examples. The abbreviation m.p. means melting point, conc. stands for "concentrated", h stands for hour(s).

EXAMPLES

Final Products 1. 3-Methyl-5-{3-[3-methyl-2-(quinolin-3-ylaminomethyl)pyridin4-ylsulfanyl]propylsulfanylmethyl}oxazolidin-2-one 4.5 g (11.32 mmol) of 5-[3-(2-chloromethyl-3-methylpyridin4-ylsulfanyl)propylsulfanylmethyl]-3-methyloxazolidin-2-one hydrochloride and 1.39 g (11.89 mmol) of 3-aminoquinoline are refluxed for 15 hours in 75 ml of isopropanol. The isopropanol is stripped off in vacuo and the residue is taken up in 100 ml of water. The pH is adjusted to 8 using saturated sodium hydrogencarbonate solution. The mixture is extracted twice with 50 ml of dichloromethane each time. The combined organic phases are concentrated. The residue is chromatographed on silica gel using toluene/ethyl acetatelmethanol/conc. ammonia=6/3.5/0.5/0.05. The crude product is digested with diethyl ether. 1.76 g (33%) of the title compound are obtained as a crystalline solid. M.p.: 98–100° C.

2. {3-Methyl4-[3-(pyrimidin-2-ylsulfanyl)propylsulfanyl]pyridin-2-ylmethyl}quinolin-3-ylamine 1.5 g (3.8 mmol) of [4-(3-chloropropylsulfanyl)-3-methylpyridin-2-ylmethyl]quinolin-3-ylamine hydrochloride are refluxed in a mixture of 25 ml of acetonitrile and 5 ml of water for 10 hours together with 0.53 g (4.7 mmol) of 2-mercaptopyrimidine and 1.21 g (11.4 mmol) of sodium carbonate. Acetonitrile is stripped off in vacuo and the residue is taken up in 100 ml of water. The mixture is extracted three times with 25 ml of dichloromethane each time. The combined organic phases are concentrated. The residue is chromatographed on silica gel using toluene/ethyl acetatelmethanol/conc. ammonia=6/3.5/0.5/0.05. The crude product is digested with diethyl ether. 1.15 g (70%) of the title compound are obtained as a crystalline solid. M.p.: 132–133° C.

3. 1,4-Bis{3-[(3-methyl4-sulfanylpyridin-2-ylmethyl)quinolin-3-ylamine]propyl}piperazine 5 g (12.67 mmol) of [4-(3-chloropropylsulfanyl)-3-methylpyridin-2-ylmethyl]quinolin-3-ylamine hydrochloride are refluxed in 100 ml of acetonitrile for 10 hours together with 6.6 g (76.07 mmol) of piperazine, 6.72 g (63.35 mmol) of sodium carbonate and a catalytic amount of sodium iodide. The mixture is then stirred at room temperature for two days. Acetonitrile is stripped off in vacuo and the residue is taken up in 100 ml of water. The mixture is extracted four times using 40 ml of dichloromethane/methanol=10/1 each time. The combined organic phases are washed twice with water and concentrated. The residue is chromatographed on silica gel using dichloromethane/methanol/triethylamine=8/2/0.1. The crude product is digested with diethyl ether. 0.24 g (5.2%) of the title compound is obtained as a crystalline solid. M.p.: 211–214° C.

4. [3-Methyl-4-(3-piperazin-1-ylpropylsulfanyl)pyridin-2-ylmethyl]quinolin-3-ylamine 5 g (12.67 mmol) of [4-(3-chloropropylsulfanyl)-3-methylpyridin-2-ylmethyl]quinolin-3-ylamine hydrochloride are refluxed in 100 ml of acetonitrile for 10 hours together with 6.6 g (76.07 mmol) of piperazine, 6.72 g (63.35 mmol) of sodium carbonate and a catalytic amount of sodium iodide. The mixture is then stirred at room temperature for two days. Acetonitrile is stripped off in vacuo and the residue is taken up in 100 ml of water. The mixture is extracted four times with 40 ml of dichloromethane/methanol=10/1 each time. The combined organic phases are washed twice with water and concentrated. The residue is chromatographed on silica gel using dichloromethane/methanol/triethylamine=8/2/0.1. The crude product is digested with diethyl ether. 3.32 g (64%) of the title compound are obtained as a crystalline solid. M.p.: 105–108° C.

5. {3-Methyl-4-[4-(pyridin4-ylmethylsulfanyl)butylsulfanyl]pyridin-2-ylmethyl}quinolin-3-ylamine 1.2 g (3.22 mol) of [4-(4-chlorobutylsuffanyl)-3-methylpyridin-2-ylmethyl]quinolin-3-ylamine and 1.51 g (6.29 mmol) of 2-pyridin-4-ylmethylisothiuronium chloride are suspended in 25 ml of ethanol. 2 ml (12 mmol) of 6 N aqueous NaOH are added dropwise in the course of 30 minutes. The mixture is stirred at room temperature for 30 minutes and then heated at 60° C. for 10 hours. After cooling, it is diluted with 100 ml of water and extracted four times with 25 ml of ethyl acetate each time. The combined organic phases are washed once with water and concentrated. The residue is chromatographed on silica gel using toluene/ethyl acetate/methanol/conc. ammonia=6/3.5/0.5/0.05. The crude product is digested with diethyl ether. 1.17 g (79%) of the title compound are obtained as a crystalline solid. M.p.: 110–113° C.

6. {3-Methyl-4-[4-(pyridin4-ylmethylsulfanyl)butoxy]pyridin-2-ylmethyl}quinolin3-ylamine 1 g (2.54 mmol) of [4-(4-chlorobutoxy)-3-methylpyridin-2-ylmethyl[]quinolin-3-ylamine hydrochloride and 1.27 g (5.29 mmol) of 2-pyridin4-ylmethylisothiuronium chloride are suspended in 20 ml of ethanol. 1.57 ml (9.42 mmol) of 6 N aqueous NaOH are added dropwise in the course of 30 minutes. The mixture is stirred at room temperature for 30 minutes and then heated at 60° C for 6 hours. After cooling, it is diluted with 100 ml of water and extracted four times with 25 ml of ethyl acetate each time. The combined organic phases are washed once with water and concentrated. The residue is chromatographed on silica gel using toluene/ethyl acetate/methanol/conc. ammonia=6/3.6/0.4/0.05. The crude product is digested with diethyl ether. 0.87 g (77%) of the title compound is obtained as a crystalline solid. M.p.: 128–129° C.

7. (3-Methyl-4-{4-[2-(2-methyl-5-nitroimidazol-1 -yl)ethylsulfanyl]butoxy}pyridin-2-ylmethyl)-quinolin-3-ylamine 1.2 g (3.05 mmol) of [4-(4-chlorobutoxy)-3-methylpyridin-2-ylmethyl]quinolin-3-ylamine hydrochloride and 1.52 g (5.73 mmol) of 2-[2-(2-methyl-5-nitroimidazol-1-yl)ethyl]isothiuronium chloride are suspended in 30 ml of ethanol. 1.91 ml (11.46 mmol) of 6 N aqueous NaOH are added dropwise in the course of 30 minutes. The mixture is stirred at room temperature for 30 minutes and then heated at 60° C. for 6 hours. After cooling, it is diluted with 100 ml of water and extracted four times using 25 ml of ethyl acetate each time. The combined organic phases are washed once with water and concentrated. The residue is chromatographed on silica gel using toluene/ethyl acetate/methanol/conc. ammonia=6/3.6/0.4/

0.05. The crude product is digested with diethyl ether. 0.64 g (41%) of the title compound is obtained as a crystalline solid. M.p.: 154–158° C.

8. {3-Methyl-4-[2-(pyridin-4-ylmethylsulfanyl) ethylsulfanyl]pyridin-2-ylmethyl}quinolin-3-ylamine 1.2 g (3.38 mmol) of [4-(2-chloroethylsulfanyl)-3-methylpyridin-2-ylmethyl]quinolin-3-ylamine and 1.76 g (7.32 mmol) of 2-pyridin-4-ylmethylisothiuronium chloride are suspended in 20 ml of ethanol. 2.44 ml (14.46 mmol) of 6 N aqueous NaOH are added dropwise in the course of 30 minutes. The mixture is stirred at room temperature for 30 minutes and then heated at 60° C. for 6 hours. After cooling, it is diluted with 80 ml of water and extracted four times using 25 ml of ethyl acetate each time. The combined organic phases are concentrated. The residue is chromatographed on silica gel using toluene/ethyl acetate/methanol/conc. ammonia=6/3.6/0.4/0.05. The crude product is digested with diethyl ether/isopropanol. 1.11 g of slightly contaminated product are obtained, which is recrystallized from 15 ml of isopropanol, and 0.84 g (56%) of the title compound is obtained as a crystalline solid. M.p.: 123–126° C.

9. (3-Methyl-4-{2-[2-(2-methyl-5-nitroimidazol-1-yl) ethylsulfanyl]ethylsulfanyl}pyridin-2-ylmethyl)quinolin-3-ylamine 1.2 g (3.38 mmol) of [4-(2-chloroethylsulfanyl)-3-methylpyridin-2-ylmethyl]quinolin-3-ylamine and 2.79 g (10.50 mmol) of 2-[2-(2-methyl-5-nitroimidazol-1-yl) ethyl]isothiuronium chloride are suspended in 25 ml of ethanol. 3.44 ml (20.64 mmol) of 6 N aqueous NaOH are added dropwise in the course of 30 minutes. The mixture is stirred at room temperature for 30 minutes and then heated at 60° C. for 6 hours. After cooling, it is diluted with 75 ml of water and extracted three times using 30 ml of ethyl acetate each time. The combined organic phases are washed once with water and concentrated. The residue is chromatographed on silica gel using toluene/ethyl acetate/methanol/conc. ammonia=6/3.8/0.2/0.05. The crude product is digested with diethyl ether. 0.52 g (31%) of the title compound is obtained as a crystalline solid. M.p.: 152–154° C.

10. {3-Methyl-4-[3-(4-pyridin-4-ylmethylpiperazin-1-yl) propylsulfanyl]pyridin-2-ylmethyl}-quinolin-3-ylamine 2 g (5.6 mmol) of [4-(3-chloropropylsulfanyl)-3-methylpyridin-2-ylmethyl]quinolin-3-ylamine and 1.3 g (7.3 mmol) of 1-pyridin-4-ylmethylpiperazine are refluxed in 20 ml of acetonitrile for 20 hours together with 3 g (28.3 mol) of sodium carbonate and a catalytic amount of sodium iodide. Acetonitrile is stripped off in vacuo and the residue is taken up in 100 ml of water. The mixture is extracted twice using 30 ml of dichloromethane/methanol=10/1 each time. The combined organic phases are washed with water and concentrated. The residue is chromatographed on silica gel using ethyl acetate/methanol/triethylamine=8.5/1.5/0.3. The crude product is digested with diethyl ether. 0.9 g (32%) of the title compound is obtained as a crystalline solid. M.p.: 145–150° C.

11. {3-Methyl-4-[3-(1-methylpiperidin-3-ylmethylsulfanyl) propylsulfanyl]pyridin-2-ylmethyl}-quinolin-3-ylamine oxalate 3.4 g (8.83 mmol) of 2-chloromethyl-3-methyl-4-[3-(1-methylpiperidin-3-ylmethylsulfanyl)propylsufanyl]-pyridine hydrochloride and 1.0 g (8.83 mmol) of 3-aminoquinoline are refluxed for 24 hours in 50 ml of acetonitrile. The acetonitrile is stripped off in vacuo and the residue is taken up in 75 ml of water. The pH is adjusted to 8 using saturated sodium carbonate solution. The mixture is extracted three times using 25 ml of dichloromethane each time. The combined organic phases are concentrated. The residue is chromatographed on silica gel using toluene/dioxane/methanol/conc. ammonia=5/4.5/0.5/0.05. The crude product is dissolved in 15 ml of hot isopropanol and treated with a solution of 1 g (11 mmol) of oxalic acid in 5 ml of isopropanol at boiling heat. The product crystallizes overnight and is then digested with diethyl ether. 0.89 g (22%) of the title compound is obtained as a crystalline solid. M.p.: 142–146° C.

12. {3-Methyl-4-[3-(pyridin-4-ylmethylsulfanyl) propylsulfanyl]pyridin-2-ylmethyl}quinolin-3-ylamine 2.5 g (7.0 mmol) of [4-(3-chloropropylsulfanyl)-3-methylpyridin-2-ylmethyl]quinolin-3-ylamine and 2.0 g (8.4 mmol) of 2-pyridin-4-ylmethylisothiuronium chloride are suspended in 25 ml of ethanol. 4.6 ml (18.4 mmol) of 4 N aqueous NaOH are added dropwise in the course of 30 minutes. The mixture is stirred at room temperature for 30 minutes and refluxed for three hours. After cooling, it is diluted with 80 ml of water and extracted three times using 25 ml of ethyl acetate each time. The combined organic phases are washed once with water and concentrated. The residue is chromatographed on silica gel using ethyl acetate/methanol/triethylamine=9.5/0.5/0.5. The crude product is digested with diethyl ether. 2.3 g (74%) of the title compound are obtained as a crystalline solid. M.p.: 116–119° C.

13. (3-Methyl-4-{4-[2-(2-methyl-5-nitroimidazol-1 -yl) ethylsulfanylbutyl]sulfanyl}pyridin-2-yl-methyl) quinolin-3-ylamine 1.5 g (3.31 mmol) of [4-(4-bromobutylsulfanyl)-3-methylpyridin-2-ylmethyl]quinolin-3-ylamine and 1.85 g (6.95 mmol) of 2-[(2-methyl-5-nitroimidazol-1-yl)ethyl] isothiuronium chloride are suspended in 30 ml of ethanol. 3.3 ml (19.8 mmol) of 6 N aqueous NaOH are added dropwise in the course of 30 minutes. The mixture is stirred at room temperature for 30 minutes and then heated at 60° C. for six hours. After cooling, it is diluted with 100 ml of water and extracted three times using 30 ml of ethyl acetate each time. The combined organic phases are concentrated. The residue is chromatographed on silica gel using toluenelethyl acetate/methanol/conc. ammonia=6/3.5/0.5/0.05. The crude product is digested with diethyl ether. 0.69 g (40%) of the title compound is obtained as a crystalline solid. M.p.: 105–109° C.

14. {4-[3-(5-Chlorothiophen-2-ylmethylsulfanyl) propylsulfanyl]-3-methylpyridin-2-ylmethyl}-quinolin-3-ylamine 2.6 g (7.2 mol) of 2-hydroxymethyl-4-[3-(5-chlorothiophen-2-ylmethylsulfanyl)propylsulfanyl]3-methylpyridine are dissolved in 8 ml of dichloromethane and cooled to 0° C. 0.8 g (10.8 mmol) of thionyl chloride and a catalytic amount of dimethylformamide are added. After 80 minutes, 20 ml of water are added dropwise and the pH is then adjusted to a value of between 8 and 9 using 2 N NaOH solution. The mixture is extracted three times using 20 ml of dichloromethane each time. The combined organic phases are washed once with water, dried over magnesium sulfate and concentrated. The intermediate thus obtained is dissolved in 20 ml of acetonitrile and treated with 2.1 g (14.5 mmol) of 3-aminoquinoline. The mixture is refluxed for 5 hours. Acetonitrile is stripped off in vacuo and the residue is taken up in 50 ml of water. The pH is adjusted to a value between 8 and 9 using saturated sodium hydrogencarbonate solution. The mixture is extracted three times using 30 ml of dichloromethane each time. The combined organic phases are washed once with water, dried over magnesium sulfate and concentrated. The residue is chromatographed on silica gel using ethyl acetate/petroleum ether=6.5/3.5. The crude product is digested with diethyl ether/diisopropyl ether=1/1. 1.1 g (31%) of the title compound are obtained as a crystalline solid. M.p.: 127–131° C.

15. (3-Methyl-4-{3-[2-(2-methyl-5-nitroimidazol-1-yl) ethylsulfanyl]propylsulfanyl}-pyridin-2-ylmethyl) quinolin-3-ylamine 1.5 g (3.43 mmol) of 2-chloromethyl-3-methyl-4-{3-[2-(2-methyl-5-nitroimidazol-1yl)ethylsulfanyl] propylsulfanyl}pyridine hydrochloride are dissolved in 30 ml of water and treated with 30 ml of dichloromethane. With vigorous stirring, the pH is adjusted to a value of 8 with saturated sodium hydrogen-carbonate solution. The organic phase is separated off. The aqueous phase is extracted again with 30 ml of dichloromethane. The combined organic phases are dried over magnesium sulfate and concentrated, and the residue is taken up in 30 ml of acetonitrile. The solution is treated with 1.51 g (10.29 mmol) of 3-aminoquinoline and refluxed for 16 hours. Acetonitrile is stripped off in vacuo and the residue is taken up in 70 ml of water. The pH is adjusted to a value of 8 using saturated sodium hydrogencarbonate solution. The mixture is extracted with 30 ml of dichloromethane. The organic phase is concentrated. The residue is chromatographed on silica gel using ethyl acetate/methanol/ conc. ammonia=18/1/0.1. The crude product is digested with diethyl ether. 0.41 g (24%) of the title compound is obtained as a crystalline solid. M.p.: 133–135° C.

16. {3-Methyl-4-[4-(pyrimidin-2-ylsulfanyl)-butoxy]-pyridin-2-ylmethyl}-quinolin-3-yl-amine The compound is obtained analogously to Example 2 from [4-(4-chloro-butoxy)-3-methyl-pyridin-2-ylmethyl]-quinolin-3-yl-amine-hydrochloride (0.9 g, 2.29 mmol) and 2-mercaptopyrimidine (0.31 g, 2.75 mmol) and Na2CO3 (0.73 g, 6.87 mmol) in 35 ml of acetonitrile. Yield: 0.81 g (82%). Mp.: 162–163° C.

17. 3-Isopropyl-5-{3-[3-methyl-2-(quinolin-3-ylaminomethyl)-pyridin-4-ylsulfanyl]-propylsulfanylmethyl}-oxazolidin-2-one The compound is obtained analogously to Example 1 from 5-[3-(2-chloromethyl-3-methyl-pyridin-4-ylsulfanyl)-propylsulfanylmethyl]-3-isopropyl-oxazolidin-2-one-hydrochloride (3.8 g, 8.39 mmol) and 3-aminoquinoline (1.1 g, 9.38 mmol). Yield:1.4 g (32%). Mp.: 100–104° C.

18. (3-Methyl-4-{3-[3-(2-methyl-4-nitro-imidazol-1-yl)-propylsulfanyl]-propylsulfanyl}-pyridin-2-ylmethyl)-quinolin-3-yl-amine The compound is obtained analogously to Example 9 from [4-(3-chloro-propylsulfanyl)-3-methyl-pyridin-2-ylmethyl]-quinolin-3-yl-amine-hydrochloride (2.0 g, 5.07 mmol) and 2-[3-(2-methyl-4-nitro-imidazol-1-yl)-propyl]-isothiourea-hydrochloride (2.4 g, 7.60 mmol). Yield: 1.92 g (72%). Mp.: 95–99° C.

19. 3-Cyclopropylmethyl-5-{3-[3-methyl-2-(quinolin-3-ylaminomethyl)-pyridin-4ylsulfanyl]-propylsulfanylmethyl}-oxazolidin-2-one The compound is obtained analogously to Example 1 from 5-[3-(2-chloromethyl-3-methyl-pyridin-4-ylsulfanyl)-propylsulfanylmethyl]-3-cyclopropylmethyl-oxazolidin-2-one-hydrochloride (5.7 g, 13.07 mmol) and 3-aminoquinoline (1.68 g, 14.38 mmol). Yield: 1.65 g (25%). Mp.: 78–81° C.

20. {3-Methyl-4-[4-(1-methyl-piperidin-3-ylmethylsulfanyl)-butoxy]-pyridin-2-ylmethyl}-quinolin-3-yl-amine 2-{4-[3-Methyl-2-(quinolin-3-ylaminomethyl)-pyridin-4yloxy]-butyl}-isothiourea-hydrochloride (0.8 g, 1.7 mmol) and 3-chloromethyl-N-methyl-piperidine (0.35 g, 1.87 mmol) are suspended in 20 ml of ethanol under an atmosphere of nitrogen. 6 N NaOH (1.13 ml, 6.8 mmol) are added during 30 minutes. The suspension is stirred for 30 minutes at room temperature and then for 6 hours at 60° C. The mixture is poured on 100 ml of water and extracted four times with 25 ml of dichloromethane. The combined organic phases are concentrated in vacuo. The residue is purified by chromatography over silica with toluene/ethyl acetate/ methanol/conc. ammonia=6/2.5/1.5/0.05. The crude product is triturated with diethyl ether to give the title compound (0.21 g, 27%). Mp.: 117–119° C.

21. {3-Methyl-4-[2-(pyridin-4-ylmethylsulfanyl)-ethoxy]-pyridin-2-ylmethyl}-quinolin-3-yl-amine The compound is obtained analogously to Examples 6, 8 and 12 from [4-(2-chloro-ethoxy)-3-methyl-pyridin-2-ylmethyl]-quinolin-3-yl-amine-hydrochloride (2.0 g, 5.49 mmol) and 2-pyridin-4-ylmethyl-isothiourea-dihydrochloride (1.98 g, 8.24 mmol). Yield: 1.59 9, (70%). Mp.: 135–136° C.

22. (3-Methyl-4-{2-[2-(2-methyl-5-nitro-imidazol-1-yl)-ethylsulfanyl]-ethoxy}-pyridin-2-ylmethyl)-quinolin-3-yl-amine The compound is obtained analogously to Example 7 from [4-(2-chloro-ethoxy)-3-methyl-pyridin-2-ylmethyl]-quinolin-3-yl-amine-hydrochloride (2.0 g, 5.49 mmol) and 2-[2-(2-methyl-5-nitro-imidazol-1-yl)-ethyl]-isothiourea-hydrochloride (2.92 g, 10.98 mmol). Yield: 0.38 g (15%). Mp.: 152–155° C.

23. (3-Methyl-4-{3-[2-(2-methyl-5-nitro-imidazol-1-yl)-ethylsulfanyl]-propoxy}-pyridin-2-ylmethyl)-quinolin-3-yl-amine The compound is obtained analogously to Example 7 from [4-(3-chloro-propoxy)-3-methyl-pyridin-2-ylmethyl]-quinolin-3-yl-amine-hydrochloride (1.30 g, 3.43 mmol) and 2-[2-(2-methyl-5-nitro-imidazol-1-yl)-ethyl]-isothiourea-hydrochloride (1.83 g, 6.87 mmol). Yield: 0.69 g (41%). Mp.: 138–141° C.

24. {3-Methyl-4-[3-(pyridin-4-ylmethylsulfanyl)-propoxy]-pyridin-2-ylmethyl}-quinolin-3-yl-amine The compound is obtained analogously to Examples 6, 8 and 12 from [4-(3-chloro-propoxy)-3-methyl-pyridin-2-ylmethyl]-quinolin-3-yl-amine-hydrochloride (1.30 g, 3.43 mmol) and pyridin-4-ylmethyl-isothiourea-dihydrochloride (1.23 g, 5.15 mmol). Yield: 0.93 g (63%). Mp.: 117–118° C.

25. 2-{3-[3-Methyl-2-(quinolin-3-ylaminomethyl)-pyridin-4-ylsulfanyl]-propylsulfanyl}-ethanol

[4-(3-Chloro-propylsulfanyl)-3-methyl-pyridin-2-ylmethyl]-quinolin-3-yl-amine-hydrochloride (1.5 g, 3.80 mmol) and 2-mercaptoethanol (0.47 g, 5.70 mmol) are suspended in 30 ml of a mixture of ethanol/water=5/1 under an atmosphere of nitrogen. 6 N NaOH (1.90 ml, 11.40 mmol) is added during 30 minutes. The mixture is refluxed for 3 hours. The mixture is poured on 150 ml of water and extracted four times with 40 ml of dichloromethane. The combined organic phases are washed with water and concentrated in vacuo. The crude product is triturated with diethylether to give the title compound (0.26 g, 17%). Mp.: 125–126° C.

26. 2-{4-[3-Methyl-2-(quinolin3-ylaminomethyl)-pyridin-4-yloxy]-butylsulfanyl}-ethanol The compound is obtained analogously to Example 25 from [4-(4-chloro-butoxy)-3-methyl-pyridin-2-ylmethyl]- quinolin-3-yl-amine-hydrochloride (1.50 g, 3.82 mmol) and 2-mercaptoethanol (0.47 g, 5.73 mmol). Yield: 0.8 g (53%). Mp.: 119–120° C.

27. 5-(4-{3-[3-Methyl-2-(quinolin-3-ylaminomethyl)-pyridin-4-ylsulfanyl]-propyl}-piperazin-1-ylmethyl)-3-pyridin-4-ylmethyl-oxazolidin-2-one The compound is obtained analogously to Example 10 from [4-(3-chloro-propylsulfanyl)-3-methyl-pyridin-2-ylmethyl]-quinolin-3-yl-amine-hydrochloride (1.50 g, 3.80 mmol) and 5-piperazin-1-ylmethyl-3-pyridin-4-ylmethyl-oxazolidin-2-one (2.1 g, 7.6 mmol). Yield: 0.57 g (25%). Mp.: 122–1280° C.

28. (3-Methyl-4-{2-[2-(pyridin-4-ylmethylsulfanyl)-ethoxy]-ethoxy}-pyridin-2-ylmethyl)-quinolin-3-yl-amine The compound is obtained analogously to Examples 6, 8 and 12 from {4-[2-(2-chloro-ethoxy)-ethoxy]-3-methyl-pyridin-2-ylmethyl}-quinolin-3-yl-amine-hydrochloride (2.0 g, 4.89 mmol) and pyridin-4-ylmethy-isothiourea-dihydrochloride (1.76 g, 7.34 mmol). Yield: 1.48 g (66%). Mp.: 62–640° C.

29. {3-Methyl-4-[3-(pyridin-2-ylmethylsulfanyl)-propylsulfanyl]-pyridin-2-ylmethyl}-quinolin-3-yl-amine The compound is obtained analogously to Example 1 from 4-[3-(pyridin-2-ylmethylsulfanyl)-propylsulfanyl]-2-chloromethyl-3-methyl-pyridine-hydrochloride (3.0 g, 7.99 mmol) and 3-aminoquinoline (0.98 g, 8.39 mmol). Yield: 0.61 g (17%). Mp.: 98–99° C.

30. (3-Methyl-4-{2-[2-(pyridin-3-ylmethylsulfanyl)-ethoxy]-ethoxy}-pyridin-2-ylmethyl)-quinolin-3-yl-amine The compound is obtained analogously to Examples 6, 8 and 12 from {4-[2-(2-chloro-ethoxy)-ethoxy]-3-methyl-pyridin-2-ylmethyl}-quinolin-3-yl-amine-hydrochloride (1.5 g, 3.67 mmol) and pyridin-3-ylmethyl-isothiourea-dihydrochloride (1.32 g, 5.51 mmol). Yield: 1.16 g (69%). Mp.: 84–86° C.

31. (3-Methyl-4-{2-[2-(pyridin-2-ylmethylsulfanyl)-ethoxy]-ethoxy}-pyridin-2-ylmethyl)-quinolin-3-yl-amine The compound is obtained analogously to Examples 6, 8 and 12 from {4-[2-(2-chloro-ethoxy)-ethoxy]-3-methyl-pyridin-2-ylmethyl}-quinolin-3-yl-amine-hydrochloride (1.5 g, 3.67 mmol) and pyridin-2-ylmethyl-isothiourea-dihydrochloride (1.32 g, 5.51 mmol). Yield: 0.84 g (50%). Mp.: 65–67° C.

32. [3-Methyl-4-(1-methyl-piperidin-3-ylmethylsulfanyl)-pyridin-2-ylmethyl]-quinolin-3-yl-amine The compound is obtained analogously to Example 1 from 2-chloromethyl-3-methyl-4-(1-methyl-piperidin-3-ylmethylsulfanyl)-pyridine-hydrochloride (3.6 g, 11.6 mmol) and 3-aminoquinoline (1.72 g, 11.9 mmol). Yield 0.63 g (14%). Mp.: 106–108° C.

33. {3-Methyl-4-[2-(pyridin-3-ylmethylsulfanyl)-ethoxy]-pyridin-2-ylmethyl}-quinolin-3-yl-amine The compound is obtained analogously to Examples 6, 8 and 12 from [4-(2-chloro-ethoxy)-3-methyl-pyridin-2-ylmethyl]-quinolin-3-yl-amine-hydrochloride (2.0 g, 5.49 mmol) and 2-pyridin-3-ylmethyl-isothiourea-dihydroclroide (1.98 g, 8.24 mmol). Yield: 1.59 g (70%). Mp.: 135–136° C.

34. {3-Methyl-4-[2-(pyridin-2-ylmethylsulfanyl)-ethoxy]-pyridin-2-ylmethyl}-quinolin-3-yl-amine The compound is obtained analogously to Examples 6, 8 and 12 from [4-(2-chloro-ethoxy)-3-methyl-pyridin-2-ylmethyl]-quinolin-3-yl-amine-hydrochloride (2.0 g, 5.49 mmol) and 2-pyridin-2-ylmethyl-isothiourea-dihydrochloride (1.98 g, 8.24 mmol). Yield: 0.62 g (27%). Mp.: 126–127° C.

35. {3-Methyl-4-[2-(pyridin-3-ylmethylsulfanyl)-ethylsulfanyl]-pyridin-2-ylmethyl}-quinolin-3-yl-amine The compound is obtained analogously to Examples 6, 8 and 12 from [4-(2-chloro-ethylsulfanyl)-3-methyl-pyridin-2-ylmethyl]-quinolin-3-yl-amine-hydrochloride (2.0 g, 5.25 mmol) and 2-pyridin-3-ylmethyl-isothiourea-dihydrochloride (1.90 g, 7.88 mmol). Yield: 1.60 g (71%). Mp.: 122–1247° C.

36. (3-Methyl-4-{2-[2,2,2-trifluoro-ethoxy)-ethylsulfanyl}-pyridin-2-ylmethyl)-quinolin-3-yl-amine hydrochloride The compound is obtained analogously to Example 1 from 2-chloromethyl-3-methyl-4-{2-[2-(2,2,2-trifluoro-ethoxy)-ethoxy]-ethylsulfanyl}-pyridine (5.0 g, 14.5 mmol) and 3-aminoquinoline (2.0 g 14.5 mmol). Yield: 0.9 g (17%). Mp.: 212–215 ° C. (decomp.)

Starting Compounds

A. 2-Chloromethyl-3-methyl-4-{3-[2-(2-methyl-5-nitroimidazol-1-yl)ethylsulfanyl]propylsulfanyl}pyridine hydrochloride A1. (3-Methyl-4-{3-[2-(2-methyl-5-nitroimidazol-1-yl)ethylsulfanyl]propylsulfanyl}pyridin-2-yl)methanol hydrochloride 1000 g (3.766 mol) of 4-(3-mercaptopropylsulfanyl)-3-methylpyridin-2-yl]methanol hydrochloride are suspended in 2.5 l of dimethylformamide. 1.4 l (7.348 mol) of sodium methoxide solution (30% strength in methanol) are added. The mixture is heated to 50° C. and stirred for one hour. Methanol is then distilled off in vacuo. 1000 ml of toluene are added and likewise distilled off in vacuo to completely remove the methanol. The suspension thus obtained is cooled to 0° C. and added dropwise at 0° C. in the course of one hour to a solution of 714 g (3.766 mol) of 1-(2-chloroethyl)-2-methyl-5-nitro-1H-imidazole in 1.2 l of dimethylformamide. The mixture is stirred at 0° C. for one hour and then at room temperature for 12 hours. 0.6 l of conc. hydrochloric acid and then 12 l of water and 1 l of dichloromethane are added. The mixture is vigorously stirred for 30 minutes. The aqueous phase is separated off and treated with 320 g of NaOH in 800 ml of water. The mixture is diluted with 10 l of water and extracted twice with 2 l of dichloromethane each time. The combined organic phases are washed with 2 l of water, then with 1 l of acetic acid (2% strength) and concentrated. The residue is treated with 0.5 l of conc. hydrochloric acid and 2 l of isopropanol. The mixture is concentrated. The residue is again treated with 2 l of isopropanol and concentrated. This process is repeated a number of times until the residue is completely crystalline. The residue is then stirred in 4 l of isopropanol, filtered off with suction and dried in vacuo. 1.08 kg (68.5%) of the title compound are obtained as a crystalline solid. M.p.: 152° C.

A2. 2-Chloromethyl-3-methyl-4-{3-[2-(2-methyl-5-nitroimidazol-1-yl)ethylsulfanyl]propylsulfanyl]pyridine hydrochloride 100 g (239 mmol) of (3-methyl-4-{3-[2-(2-methyl-5-nitroimidazol-1-yl)ethylsulfanyl]propylsulfanyl}pyridin-2-yl)methanol hydrochloride are suspended in a mixture of 500 ml of dichloromethane and 50 ml of dimethylformamide. 30 ml (413 mmol) of thionyl chloride in 50 ml of dichloromethane are slowly added dropwise at 5–10° C. The mixture is stirred at 5–10° C. for 12 hours and at room temperature for a further 4 hours. 100 ml of isopropanol are added. The mixture is completely concentrated in vacuo. The residue is taken up in 500 ml of isopropanol and stirred at room temperature for 12 hours. The title compound crystallizes out, and is filtered off with suction and dried in vacuo. 64 g (62%) of the title compound are obtained as a crystalline solid, which is used without further purification.

B. 2-Hydroxymethyl-4-[3-(5-chlorothiophen-2-ylmethylsulfanyl)propylsulfanyl]-3-methyl-pyridine 6.9 g (26 mmol) of [4-(3-mercaptopropylsulfanyl)-3-methylpyridin-2-yl]methanol hydrochloride and 4.4 g (26 mmol) of 2-chloro-5-chloromethylthiophene are stirred in 100 ml of dimethylformamide for two hours together with 14 g (132 mmol) of sodium carbonate. The mixture is diluted with 100 ml of water and extracted three times with 30 ml of ethyl acetate. The combined organic phases are dried over magnesium sulfate and concentrated. The residue is chromatographed on silica gel using ethyl acetate/petroleum ether/triethylamine=8/2/0.3. 5.9 g (63%) of the title compound are obtained as a crystalline solid, which is used without further purification.

C. [4-(4-Bromobutylsulfanyl)-3-methylpyridin-2-ylmethyl]quinolin-3-ylamine

C1. [4-(4-Bromobutylsulfanyl)-3-methylpyridin-2-yl]methanol 50 g (185 mmol) of 2-(2-hydroxymethyl-3-methylpyridin-4-yl)isothiuronium chloride are dissolved in a mixture of 270 ml of ethanol and 130 ml of water under a nitrogen atmosphere. 160 g (740 mmol) of 1,4-dibromobutane are added. 126.5 ml of a 6 N sodium hydroxide solution are added dropwise in the course of 45 minutes. The mixture is stirred at 50° C. for 24 hours. It is concentrated in vacuo and the residue is diluted with 400 ml of water. The mixture is extracted three times using 50 ml of dichloromethane each time. The combined organic phases are washed with water and concentrated. The residue is taken up again in 400 ml of water. The pH is adjusted to 8 using saturated aqueous sodium hydrogencarbonate solution. The mixture is extracted three times using 300 ml of toluene each time. The combined organic phases are washed with water, dried over magnesium sulfate and concentrated. The residue is chromatographed on silica gel using ethyl acetatelmethanol/conc. ammonia=19/1/0.1. 11.67 g (22%) of the title compound are obtained as a yellow oil, which is used without further purification.

C2. 4-(4-Bromobutylsulfanyl)-2-chloromethyl-3-methylpyridine hydrochloride 11.5 g (39.62 mmol) of [4-(4-bromobutylsulfanyl)-3-methylpyridin-2-yl]methanol are dissolved in 75 ml of dichloromethane and treated with 7.07 g (59.43 mmol) of thionyl chloride in 20 ml of dichloromethane in the course of 20 minutes. The mixture is stirred at room temperature for 2 hours. It is concentrated in vacuo and the residue is coevaporated twice with 50 ml of toluene each time. The crude product is digested with diethyl ether. 11.97 g (88%) of the title compound are obtained as a crystalline solid, which is used without further purification.

C3. [4-(4-Bromobutylsulfanyl)-3-methylpyridin-2-ylmethyl]quinolin-3-ylamine 5 g (14.5 mmol) of 4-(4-bromobutylsulfanyl)-2-chloromethyl-3-methylpyridine hydrochloride are refluxed in 50 ml of isopropanol for three days together with 2 g (17.3 mmol) of 3-aminoquinoline. The title compound crystallizes out on cooling. It is filtered off with suction and washed twice with 20 ml of isopropanol each time. 3.62 g (55%) of the title compound are obtained as a crystalline solid, which is used without further purification.

D. [4-(3-Chloropropylsulfanyl)-3-methylpyridin-2-ylmethyl]quinolin-3-ylamine 13 g (46 mmol) of [4-(3-chloropropylsulfanyl)-2-chloromethyl-3-methylpyridine hydrochloride are refluxed in 130 ml of isopropanol for three days together with 10.2 g (69 mmol) of 3-aminoquinoline. The crude product crystallizes out on cooling. It is filtered off with suction and washed twice with 30 ml of isopropanol each time. The crude product is taken up in 150 ml of water and the free base is liberated using saturated sodium hydrogencarbonate solution. The mixture is extracted three times using 30 ml of ethyl acetate each time. The combined organic phases are dried over magnesium sulfate and concentrated. The residue is chromatographed on silica gel using ethyl acetate/petroleum ether/triethylamine=6/4/0.2. 8.3 g (50%) of the title compound are obtained as a crystalline solid, which is used without further purification.

E. 2-Chloromethyl-3-methyl-4-[3-(1-methylpiperidin-3-ylmethylsulfanyl)propylsulfanyl]-pyridine hydrochloride E1. 2-Hydroxymethyl-3-methyl-4-[3-(1-methylpiperidin-3-ylmethylsulfanyl)propylsulfanyl]-pyridine hydrochloride 10 g (37.6 mmol) of [4-(3-mercaptopropylsulfanyl)-3-methylpyridin-2-yl]methanol hydrochloride and 6.58 g (35.73 mmol) of 3-chloromethyl-N-methylpiperidine hydrochloride are stirred in 70 ml of dimethylformamide at 50° C. for 5 hours together with 26 g (188 mmol) of potassium carbonate. Dimethylformamide is stripped off in a high vacuum. The residue is diluted with 200 ml of water and extracted five times with 50 ml of ethyl acetate. The combined organic phases are washed with water, dried over magnesium sulfate and concentrated. The residue is chromatographed on silica gel using ethyl acetate/methanol/conc. ammonia=6/1/0.1. 8 g (63%) of the title compound are obtained as a yellow oil, which is used without further purification.

E2. 2-Chloromethyl-3-methyl-4-[3-(1-methylpiperidin-3-ylmethylsulfanyl)propylsulfanyl]-pyridine hydrochloride 3 g (8.83 mmol) of 2-hydroxymethyl-3-methyl-4-[3-(1-methylpiperidin-3-ylmethylsulfanyl)-propylsulfanyl]pyridine hydrochloride are dissolved in 50 ml of dichloromethane and treated with 1.26 g (10.6 mmol) of thionyl chloride in 10 ml of dichloromethane. The mixture is stirred at room temperature for two hours. It is then concentrated in vacuo and coevaporated twice with 30 ml of toluene each time. The residue is dried in vacuo. 3.5 g (100%) of the title compound are obtained as a green oil, which is used without further purification.

F. 1-Pyridin-4-ylmethylpiperazine 8 g (47 mmol) of 4-chloromethylpyridine hydrochloride and 12.5 g (145 mmol) of piperazine are boiled in 110 ml of acetonitrile for 12 hours together with 19.3 g (140 mmol) of potassium carbonate and a catalytic amount of sodium iodide. The potassium carbonate is filtered off and the mixture is concentrated. The residue is chromatographed on silica gel using ethyl acetate/methanol/triethylamine=5.5/4.5/0.5. 5.4 g (65%) of the title compound are obtained as a yellow oil, which is used without further purification.

G. [4-2-Chloroethylsulfanyl)-3-methylpyridin-2-ylmethyl]quinolin-3-yl amine 5 g (18.34 mmol) of 4-(2-chloroethylsulfanyl)-2-chloromethyl-3-methylpyridine hydrochloride are refluxed in 50 ml of isopropanol for 4 days together with 2.56 g (22 mmol) of 3-aminoquinoline. The precipitate is filtered off with suction and taken up in 100 ml of water, and the free base is liberated using aqueous sodium hydrogencarbonate solution. The mixture is extracted three times using 50 ml of di-chloromethane each time. The combined organic phases are washed with water, dried over magnesium sulfate and concentrated. The crude product is digested with diethyl ether. 2.83 g (45%) of the title compound are obtained as a crystalline solid. M.p.: 114–117° C.

H. [4-(4-Chlorobutoxy)-3-methylpyridin-2-ylmethyl]quinolin-3-ylamine hydrochloride H1. 4-(4-Hydroxybutoxy)-2,3-dimethylpyridine N-oxide 24.4 g (609.1 mmol) of sodium hydride (60% strength in paraffin) are added in portions to 320.2 g (3.55 mmol) of butanediol under a nitrogen atmosphere. The mixture is stirred at room temperature for 2 days. The mixture is heated to 100° C. and 4-chloro-2,3-dimethylpyridine N-oxide is added. The mixture is stirred first at 100° C. for 2 h and then at 120° C. for a further 2 h. It is then concentrated in a high vaccum. The residue is suspended in 600 ml of ethanol and heated. After filtering off the inorganic salts with suction, the filtrate is concentrated. The residue is purified by chromatography on silica gel (eluent: ethyl acetate→ethyl acetate:methanol=9:1). the eluent is concentrated. The residue is then digested with diethyl ether. After filtration and drying of the precipitate, 67.4 g (63%) of the title compound are obtained as a colorless solid, which is used without further purification.

H2. 4-(2-Hydroxymethyl-3-methylpyridin-4-yloxy)butan-1-ol 30 g (0.14 mol) of 4-(4-hydroxybutoxy)-2,3-dimethylpyridine N-oxide are added in portions at 50° C. to acetic anhydride in the course of 1 h. After addition is complete, the mixture is heated to 90° C. and stirred for a further 8 h. The mixture is then concentrated. The residue obtained is dissolved in 150 ml of methanol and 38.3 g (0.71 mol) of sodium methoxide solution (30% strength in methanol) are added. The mixture is stirred at room temperature for 1 h. It is then concentrated. The residue is taken up in half-saturated sodium chloride solution and dichloromethane with vigorous stirring. The aqueous phase is extracted using 3×50 ml of dichloromethane. The organic extracts are dried over magnesium sulfate and concentrated. The residue is digested with diethyl ether. After filtration and drying of the precipitate, 21.6 g (72%) of the title compound are obtained. M.p.: 61–63° C.

H3. 4-(4-Chlorobutoxy)-2-chloromethyl-3-methylpyridine hydrochloride

A solution of 33.8 g (284 mmol) of thionyl chloride in 25 ml of dichloromethane is added dropwise in the course of 30 minutes with ice-cooling to a solution of 15 g (71 mmol) of 4-(2-hydroxymethyl-3-methylpyridin-4-yloxy)butan-1-ol in 200 ml of anhydrous dichloromethane. The mixture is then warmed to room temperature and stirred for 20 h. The mixture is then concentrated and coevaporated with 3×20 ml of toluene. The precipitate obtained is digested with diethyl ether. After filtration and drying, 20.8 g (100%) of the title compound are obtained. This product is employed directly for further reaction without additional purification.

H4. [4-(4-Chlorobutoxy)-3-methylpyridin-2-ylmethyl] quinolin-3-ylamine hydrochloride 5 g (17.56 mmol) of 4-(4-chlorobutoxy)-2-chloromethyl-3-methylpyridine hydrochloride are refluxed in 75 ml of isopropanol for 18 hours together with 2.46 g (21.08 mmol) of 3-aminoquinoline. The precipitate is filtered off with suction and washed with isopropanol. The crude product is digested with diethyl ether. 3.3 g (48%) of the title compound are obtained as a crystalline solid. M.p.: 219–223° C.

I. [4-(4-Chlorobutylsulfanyl)-3-methylpyridin-2-ylmethyl] quinolin-3-ylamine

I1. 2-(2-Hydroxymethyl-3-methylpyridin-4-yl) isothiuronium chloride 40 g (206 mmol) of 4-chloro-2-hydroxymethyl-3-methylpyridine hydrochloride are refluxed in 400 ml of acetone for 14 hours together with 18.9 g (248 mmol) of thiourea. The mixture is then cooled to 0° C. and the precipitated solid is filtered off with suction. The solid is washed in the cold in 200 ml of ethanol with stirring, filtered off with suction and dried in vacuo. 53.5 g (96%) of the title compound are obtained as a crystalline solid, which is used without further purification.

I2. 4-(2-Hydroxymethyl-3-methylpyridin-4-ylsulfanyl) butan-1-ol 50 g (185 mmol) of 2-(2-hydroxymethyl-3-methylpyridin-4-yl)isothiuronium chloride are dissolved in a mixture of 200 ml of ethanol and 100 ml of water and purged with nitrogen. 83 g (740 mmol) of 4-chloro-1-butanol are added. 126.5 ml of a 6 N sodium hydroxide solution are added dropwise in the course of 45 minutes. The mixture is stirred at room temperature for three days. It is concentrated in vacuo and the residue is diluted with 500 ml of water. The mixture is extracted three times using 50 ml of dichloromethane each time. The combined organic phases are washed with water and concentrated. The residue is taken up again in 400 ml of water. The pH is adjusted to about 1 using HCl. The mixture is extracted twice using 50 ml of ethyl acetate each time in order to remove excess 4-chloro-1-butanol. The pH of the aqueous phase is adjusted to about 10 using NaOH. The mixture is extracted three times using 100 ml of dichloromethane each time. The combined organic phases are washed with water, dried over magnesium sulfate and concentrated. The residue is chromatographed on silica gel using toluene/dioxane/conc. ammonia=1/1/0.05. 21.8 g (52%) of the title compound are obtained as a crystalline solid, which is used without further purification.

I3. 4-(4-Chlorobutylsulfanyl)-2-chloromethyl-3-methylpyridine hydrochloride 15 g (49.9 mmol) of 4-(2-hydroxymethyl-3-methylpyridin-4-ylsulfanyl)butan-1-ol are dissolved in 200 ml of dichloromethane. 19.8 g (166.5 mmol) of thionyl chloride are slowly added dropwise. The mixture is stirred at room temperature for 24 hours. It is concentrated and coevaporated three times with 100 ml of toluene. The crystalline residue is digested with diethyl ether. 19.8 g (99%) of the title compound are obtained as a crystalline solid. M.p.: 154–1570° C.

I4. [4-(4Chlorobutylsulfanyl)-3-methylpyridin-2-ylmethyl] quinolin-3-ylamine 4.5 g (15 mmol) of 4-(4-chlorobutylsulfanyl)-2-chloromethyl-3-methylpyridine hydrochloride are refluxed in 50 ml of isopropanol for three days together with 2.1 g (18 mmol) of 3-aminoquinoline. Isopropanol is stripped off in vacuo and the residue is taken up in 100 ml of water and the free base is liberated using aqueous sodium hydrogencarbonate solution. The mixture is extracted four times using 25 ml of dichloromethane each time. The combined organic phases are washed with water, dried over magnesium sulfate and concentrated. The residue is chromatographed on silica gel using toluene/ethyl acetate/methanol/conc. ammonia=6/3.5/0.5/0.05. The crude product is digested with diethyl ether. 2.39 g (43%) of the title compound are obtained as a crystalline solid. m.p.: 126–127° C.

J. 5-[3-(2-Chloromethyl-3-methylpyridin-4-ylsulfanyl) propylsulfanylmethyl]-3-methyloxazolidin-2-one hydrochloride J1. 5-[3-(2-Hydroxymethyl-3-methylpyridin-4-ylsulfanyl) propylsulfanylmethyl]-3-methyloxazolidin-2-one 7.5 g (28.2 mmol) of [4-(3-mercaptopropylsulfanyl)-3-methylpyridin-2-yl]methanol hydrochloride and 7.7 g (31 mmol) of 5-chloromethyl-3-methyloxazolidin-2-one are stirred at 60° C. in 100 ml of dimethylformamide for three hours together with 11.7 g (84.7 mmol) of potassium carbonate. Dimethylformamide is stripped off in a high vaccum and the residue is taken up in 100 ml of water. The mixture is extracted four times using 30 ml of dichloromethane each time. The combined organic phases are washed with water, dried over magnesium sulfate and concentrated. The residue is chromatographed on silica gel using toluene/dioxane/methanol/conc. ammonia=5/4/1/0.05. 8.1 g (84%) of the title compound are obtained as a colorless oil, which is used without further purification.

J2. 5-[3-(2-Chloromethyl-3-methylpyridin-4-ylsufanyl)propylsulfanylmethyl]-3-methyloxazolidin-2-one hydrochloride 8 g (23.3 mmol) of 5-[3-(2-hydroxymethyl-3-methylpyridin-4-ylsulfanyl)propylsulfanylmethyl]-3-methyl-oxazolidin-2-one are dissolved in 80 ml of dichloromethane and treated with a solution of 3.05 g (25.63 mmol) of thionyl chloride in 20 ml of dichloromethane in the course of 30 minutes. The mixture is stirred at room temperature for one hour. It is concentrated and coevaporated three times with 30 ml of toluene. 9.25 g (100%) of the title compound are obtained as a yellow oil, which is used without further purification.

K. 5-[3-(2-Chloromethyl-3-methyl-pyridin-4-ylsuffanyl)-propylsulfanylmethyl]-3-isopropyl-oxazolidin-2-one-hydrochloride The compound is obtained analogously to Example J, starting with 5chloromethyl-3-isopropyl-oxazolidin-2-on and [4-(3-mercapto-propylsulfanyl)-3-methyl-pyridin-2-yl]-methanol-hydrochloride.

L. 5-[3-(2-Chloromethyl-3-methyl-pyridin-4-ylsulfanyl)-propylsulfanylmethyl]-3-cyclopropyl-methyl-oxazolidin-2-one-hydrochloride The compound is obtained analogously to Example J, starting with 5-chloromethyl-3-cyclopropylmethyl-oxazolidin-2-on and [4-(3-mercapto-propylsulfanyl)-3-methyl-pyridin-2-yl]-methanol-hydrochloride.

M. 2-{4-[3-Methyl-2-(quinolin-3-ylaminomethyl)-pyridin-4-yloxy]-butyl}-isothiourea-hydrochloride

[4-(4-Chloro-butoxy)-3-methyl-pyridin-2-ylmethyl]-quinolin-3-yl-amine-hydrochioride (1 g, 2.54 mmol) and thiourea (0.6 g, 7.64 mmol) are refluxed in 30 ml of isopropanol for 12 hours. The crystalline product is filtered off and triturated with diethyl ether to give the title compound (0.87 g, 73%).

N. [4-(2-Chloro-ethoxy)-3-methyl-pyridin-2-ylmethyl]-quinolin-3-yl-amine-hydrochloride The compound is obtained analogously to Example H, starting with ethylenglycol and 4-chloro-2,3-dimethyl-pyridine-N-oxide.

O. [4-(3-Chloro-propoxy)-3-methyl-pyridin-2-ylmethyl]-quinolin-3-yl-amine-hydrochloride The compound is obtained analogously to Example H, starting with 1,3-propandiol and 4-chloro-2,3-dimethyl-pyridine-N-oxide.

P. 5-Piperazin-1-ylmethyl-3-pyridin-4-ylmethyl-oxazolidin-2-one

P1. 5-Chloromethyl-3-pyridin-4-ylmethyl-oxazolidin-2-one

Sodium hydride (5.8 g, 0.242 mol) is suspended in 200 ml of NMP (N-methylpyrrolidone) under an atmosphere of nitrogen. A solution of (±)-5-chloromethyl-2-oxazolidinone (15 g, 0.110 mol) in 60 ml of NMP is added slowly during 45 minutes. The mixture is stirred for one hour at room temperature. 4-Picolylchloride-hydrochloride (20.46 g, 0.121 mol) is added in small portions during one hour. The mixture is stirred for 18 hours at room temperature. NMP is evaporated in vacuo. The residue is diluted with 250 ml of water and extracted four times with 50 ml of dichloromethane. The combined organic phases are washed with water and concentrated in vacuo. The residue is purified by chromatography over silica with ethyl acetate/methanol=15/1 to yield the title compound as yellow oil (24 g, 96%).

P2. 5-Piperazin-1-ylmethyl-3-pyridin-4-ylmethyl-oxazolidin-2-one

5-Chloromethyl-3-pyridin-4-ylmethyl-oxazolidin-2-one (18 g, 79.41 mmol), piperazine (35 g, 397 mmol) and $K_2CO_3$ (55 g, 397 mmol) are refluxed in 350 ml of acetonitril together with a catalytic amount of sodium iodide for 24 hours. The mixture is filtered and the acetonitril is evaporated in vacuo. The residue is purified by chromatography over silica with ethyl acetate/methanol=15/1 to yield the title compound as yellow oil (24 g, 96%).

Q. {4-[2-(2-Chloro-ethoxy)-ethoxy]-3-methyl-pyridin-2-ylmethyl}-quinolin-3-yl-amine-hydrochloride The compound is obtained analogously to Example H, starting with diethylenglycol and 4-chloro-2,3-dimethyl-pyridine-N-oxide.

R. 4-[3-(pyridin-2-ylmethylsulfanyl)-propylsulfanyl]-2-chloromethyl-3-methyl-pyridine-hydrochloride R1. 4-[3-(pyridin-2-ylmethylsulfanyl)-propylsulfanyl]-2-hydroxymethyl-3-methyl-pyridine

[4-(3-Mercapto-propylsulfanyl)-3-methyl-pyridin-2-yl]-methanol-hydrochloride (20.0 g, 75.38 mmol), 2-picolylchloride (13.39 g, 79.15 mmol) and $K_2CO_3$ (52.0 g, 377 mmol) are stirred in 200 ml of DMF under an atmosphere of nitrogen for three hours. The mixture is filtered and concentrated in vacuo. The residue is purified by chromatography over silica with toluenelethyl acetate/methanol/conc. ammonia=6/3.5/0.5/0.05 to give the title compound as yellow oil (17.21 g, 71%).

R2. 4-[3-(pyridin-2-ylmethylsulfanyl)-propylsulfanyl]-2-chloromethyl-3-methyl-pyridine-hydrochloride 4-[3-(Pyridin-2-ylmethylsulfanyl)-propylsulfanyl]-2-hydroxymethyl-3-methyl-pyridine (17 g, 53.04 mmol) is dissolved in 170 ml of dichloromethane. Thionylchloride (7..57 g, 63.65 mmol) in 30 ml of dichloromethane is added slowly. The mixture is stirred for two hours at room temperature and afterwards concentrated in vacuo to give the crude title compound which is used directly in the next step without further purification.

S. 2-Chloromethyl-3-methyl-4-(1-methyl-piperidin-3-ylmethylsulfanyl)-pyridine-hydrochloride S1. [3-Methyl-4-(1-methyl-piperidin-3-ylmethylsulfanyl)-pyridin-2-yl]-methanol The compound is obtained analogously to Example 5. from 2-(2-hydroxymethyl-3-methyl-pyridin-4-yl)-isothiourea-hydrochloride (15 g, 55.5 mmol) and 3-chloromethyl-N-methylpiperidine (11.5 g, 61.07 mmol). Yield: 2.86 g (20%).

S2. 2-Chloromethyl-3-methyl-4-(1-methyl-piperidin-3-ylmethylsulfanyl)-pyridine-hydrochloride The compound is obtained analogously to Example R2. from [3-methyl4-(1-methyl-piperidin-3-ylmethylsulfanyl)-pyridin-2-yl]-methanol (2.8 g, 10.92 mmol) and thionylchloride (2 g, 16.38 mol). Yield: 3.39 g (100%).

T. 2-Chloromethyl-3-methyl-4-{2-[2-(2,2,2-trifluoroethoxy)-ethoxy]-ethylsulfanyl}-pyridine T1. Toluene-4-sulfonic acid 2-[2-(2,2,2-trifluoro-ethoxy)-ethoxy]-ethyl ester To a solution of 2-[2-(2,2,2-trifluoro-ethoxy)-ethoxy]-ethanol (3.0 g, 15.9 mmol) in pyridine (15 ml) 4-toluenesulfonyl chloride (3.2 g, 16.8 mmol) is added in small portions. After stirring for 1 h at room temperature, the solvent is evaporated. The residue is dissolved in ethyl acetate (50 ml) and extracted with water (50 ml). The aqueous phase is extracted with ethyl acetate (3×50 ml) and subsequently the combined organic extracts are washed with water (50 ml), dried over magnesium sulphate and evaporated. The residing yellow oil (4.0 g, 76%) is used without further purification for the next step.

T2. (3-Methyl-4-{2-[2-(2,2,2-trifluoro-ethoxy)ethoxy]-ethylsulfanyl}-pyridin-2-yl)-methanol To a solution of toluene-4-sulfonic acid 2-[2-(2,2,2-trifluoro-ethoxy)-ethoxy]-ethyl ester (1.3 g, 15.9 mmol) in ethanol (10 ml) 2-(2-hydroxymethyl-3-methyl-pyridin-4yl)-isothiuronium chloride (1.1 g, 4.7 mmol) is added and then, under a nitrogen atmosphere, an aqueous solution of 6N sodium hydroxide (5 ml, 30 mmol) is added dropwise over a period of 30 minutes at room temperature. After stirring the suspension for 1 h the solvent is evaporated and the residue dissolved in ethyl acetate (30 ml) and water (30 ml). The aqueous phase is extracted with ethyl acetate (3×30 ml) and the combined organic extracts are washed with water, dried over magnesium sulphate and evaporated. The residue is purified by silica gel chromatography (eluent: toluene/ethyl acetate=1:1). After evaporating the combined fractions with Rf=0.46 the title compound is isolated as an amorphous solid (0.85 g, 64%) which is used without further purification for the next step.

T3. 2-Chloromethyl-3-methyl-4-{2-[2-(2,2,2-trifluoro-ethoxy)ethoxy]-ethylsulfanyl}-pyridine To a solution of (3-methyl-4-{2-[2-(2,2,2-trifluoro-ethoxy)-ethoxy]-ethylsulfanyl}-pyridin-2-yl)-methanol (0.8 g, 2.46 mmol) in dichloromethane (10 ml) a solution of thionyl chloride (0.4 g, 3.42 mmol) in dichloromethane (5 ml) is added dropwise at 4° C. over a period of 20 minutes. After stirring the solution for additional 30 minutes at room temperature, water (20 ml) is added and the mixture is neutralised by the addition of solid NaHCO3 with vigorous stirring. The aqueous phase is separated and extracted with ethyl acetate (3×20 ml). The combined organic phases are washed with water, dried over magnesium sulphate and evaporated. The title compound is isolated as an amorphous solid (0.84 g, 99%) which is used directly for the preparation of final products.

COMMERCIAL UTILITY

The excellent activity of compounds of the formula I and their salts against Helicobacter bacteria allows their use in human medicine as active compounds for the treatment of illnesses which are based on Helicobacter bacteria.

The invention therefore further relates to a process for the treatment of mammals, in particular humans, who are suffering from illnesses which are based on Helicobacter bacteria. The process comprises administering to the sick individual a therapeutically efficacious and pharmacologically tolerable amount of one or more compounds of the formula I and/or their pharmacologically tolerable salts.

The invention moreover relates to the compounds of the formula I and their pharmacologically tolerable salts for use in the treatment of illnesses which are based on Helicobacter bacteria.

The invention also comprises the use of compounds of the formula I and their pharmacologically tolerable salts in the production of medicaments which are employed for the control of those illness which are based on Helicobacter bacteria.

The invention further relates to medicaments for the control of Helicobacter bacteria, which contain one or more compounds of the general formula I and/or their pharmacologically tolerable salts.

Of the Helicobacter strains against which the compounds of the formula I prove active, the strain Helicobacter pylori may be mentioned in particular.

The medicaments are prepared by processes known per se, which are familiar to the person skilled in the art. As medicaments, the pharmacologically active compounds of the formula I and their salts (=active compounds) are either used as such, or preferably employed in combination with suitable pharmaceutical auxiliaries, e.g. in the form of tablets, coated tablets, capsules, emulsions, suspensions, gels or solutions, the active compound content advantageously being between 0.1 and 95%.

Auxiliaries which are suitable for the desired pharmaceutical formulations are familiar to the person skilled in the art on account of his/her expert knowledge. In addition to solvents, gel-forming agents, tablet auxiliaries and other active compound carriers, it is possible to use, for example, antioxidants, dispersants, emulsifiers, antifoams, flavor corrigents, preservatives, solubilizers, colorants or permeation promoters and complexing agents (e.g. cyclodextrins).

The active compounds can be administered, for example, parenterally (e.g. intravenously) or in particular orally.

In general, the active compounds are administered in human medicine in a daily dose of approximately 0.2 to 50, preferably 1 to 30, mg/kg of body weight, if appropriate in the form of a number of, preferably 2 to 6, individual doses to achieve the desired result.

The compounds according to the invention can also be administered in a fixed or free combination together with a substance neutralizing gastric acid and/or inhibiting gastric acid secretion and/or with a substance suitable for the conventional control of Helicobacter pylori.

Substances neutralizing gastric acid which may be mentioned are, for example, sodium hydrogencarbonate or other antacids (such as aluminum hydroxide, magnesium aluminate or magaldrate). Substances inhibiting gastric acid secretion which may be mentioned are, for example, $H_2$ blockers (e.g. cimetidine, ranitidine), $H^+/K^+$ ATPase inhibitors (e.g. lansoprazole, omeprazole, rabeprazole or, in particular, pantoprazole) and so-called peripheral anticholinergics (e.g. pirenzepine, telenzepine).

Substances suitable for the conventional control of Helicobacter pylori which may be mentioned are, in particular, antimicrobially active substances such as, for example, penicillin G, gentamycin, erythromycin, clarithromycin, azithromycin, nitrofurazone, tinidazole, nirofurantoin, furazolidone, metronidazole or amoxycillin, or else alternatively bismuth salts such as, for example, bismuth citrate.

BIOLOGICAL INVESTIGATIONS

The compounds of the formula I were investigated with respect to their activity against Helicobacter pylori following the method described by Tomoyuki Iwahi et al. (Antimicrobial Agents and Chemotherapy, 1991, 490–496) using Columbia agar (Oxoid) and a growth period of 4 days. For the compounds the approximate MIC 50 values listed in Table A below resulted here (the numbers of the indicated agree with the example numbers in the description).

TABLE A

| Compound No. | Appr. MIC 50 ($\mu$g/ml) |
| --- | --- |
| 1 | ≦0.1 |
| 2 | ≦0.1 |
| 6 | ≦0.1 |
| 7 | ≦0.1 |
| 8 | ≦0.1 |
| 9 | ≦0.1 |

TABLE A-continued

| Compound No. | Appr. MIC 50 (μg/ml) |
|---|---|
| 10 | ≦0.1 |
| 11 | ≦0.1 |
| 12 | ≦0.1 |
| 13 | ≦0.1 |
| 14 | ≦0.1 |
| 15 | ≦0.1 |
| 16 | ≦0.1 |
| 17 | ≦0.1 |
| 18 | ≦0.1 |
| 19 | ≦0.1 |
| 20 | ≦0.1 |
| 21 | ≦0.1 |
| 22 | ≦0.1 |
| 23 | ≦0.1 |
| 24 | ≦0.1 |
| 25 | ≦0.1 |
| 26 | ≦0.1 |
| 27 | ≦0.1 |
| 28 | ≦0.1 |
| 29 | ≦0.1 |
| 30 | ≦0.1 |
| 31 | ≦0.1 |
| 32 | ≦0.1 |
| 33 | ≦0.1 |
| 34 | ≦0.1 |
| 35 | ≦0.1 |
| 36 | ≦0.1 |

What is claimed is:

1. A compound of the formula I

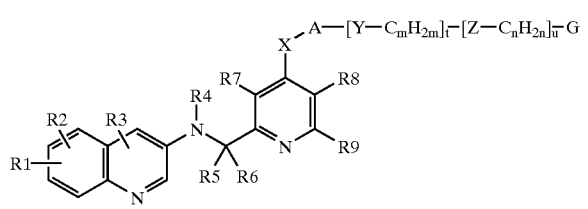

(I)

in which

R1, R2 and R3 are identical to or different from one another and are hydrogen, 1–4C-alkyl, 1–4C-alkoxy, hydroxyl, halogen, carboxyl or 1–4C-alkylthio, R4 is hydrogen or 1–4C-alkyl, R5 is hydrogen or 1–4C-alkyl, R6 is hydrogen or 1–4C-alkyl, R7 is hydrogen, 1–4C-alkyl, 1–4C-alkoxy or halogen, R8 is hydrogen, 1–4C-alkyl, 1–4C-alkoxy or halogen, R9 is hydrogen or 1–4C-alkyl, A is 1–7C-alkylene, 2–7C-alkenylene, 3–7C-cycloalkylene or phenylene, G is hydrogen, 1–7C-alkyl, 1–4C-alkyl which is completely or mainly substituted by fluorine, 2–7C-alkenyl, 3–7C-cycloalkyl, a mono- or di-1–4C-alkylcarbamoyl or -thiocarbamoyl radical, an N-1–4C-alkyl-N'-cyanoamidino radical, a 1-N-1–4C-alkylamino-2-nitroethylene radical, an N-2-propynyl-N'-cyanoamidino radical, an aminosulfonylamidino radical, the radical —N(R10)R11, the part of the compound of the above formula I bonded to A (including X and via X) or a cyclic system or bicyclic system which is unsubstituted or substituted by R12 and R13 and which is selected from the group consisting of benzene, naphthalene, furan, thiophene, pyrrole, oxazole, oxazoline, oxazolidinone, isoxazole, thiazole, thiazoline, isothiazole, imidazole, imidazoline, pyrazole, triazole, tetrazole, thiadiazole, thiadiazole 1-oxide, oxadiazole, pyridine, pyridine N-oxide, pyrimidine, halopyrimidine, piperidine, triazine, pyridone, benzimidazole, imidazopyridine, benzothiazole, benzoxazole, quinoline and imidazopyridazine, in which R10 is 1–7C-alkyl, 3–7C-cycloalkyl or Ar-1–4C-alkyl and R11 is 1–7C-alkyl, 3–7C-cycloalkyl or Ar-1–4C-alkyl, where Ar is phenyl, furyl, naphthyl, tetrahydronaphthyl or phenyl which is substituted by R14, R15 and R16, or in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino radical is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino radical can be substituted in the 2-, 3-, 5- or 6-position by a 1–4C-alkyl radical, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl, a substituted morpholino radical is substituted by one or two identical or different 1–4C-alkyl radicals, a substituted thiomorpholino radical is substituted by one or two identical or different 1–4C-alkyl radicals or a carboxyl group, a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C-alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 3–7C-cycloalkyl, 1–4C-alkoxy, carboxyl, 1–4C-alkoxycarbonyl, pyridinyl or —N(R18)R19, where R18 is hydrogen, 1–4C-alkyl or —CO—R20 and R19 is hydrogen or 1–4C-alkyl, or where R18 and R19, together and including the nitrogen atom to which both are bonded, are a piperidino or morpholino radical, R20 is hydrogen, 1–4C-alkyl or 1–4C-alkoxy, X is O (oxygen), N-1–4C-alkyl, NH or S, Y is O (oxygen), N-1–4C-alkyl, NH, S, 1,4-piperazinylene or 1,4-piperidinylene, Z is O (oxygen), N-1–4C-alkyl, NH or S or CO, m is a number from 1 to 7, n is a number from 0 to 4, t is the number 0 or 1 and u is the number 0 or 1, or its salts.

2. A compound of the formula I as claimed in claim 1 in which

R1, R2 and R3 are identical to or different from one another and are hydrogen, 1–4C-alkyl, 1–4C-alkoxy, hydroxyl, halogen, carboxyl or 1–4C-alkylthio, R4 is hydrogen or 1–4C-alkyl, R5 is hydrogen or 1–4C-alkyl, R6 is hydrogen or 1–4C-alkyl, R7 is hydrogen, 1–4C-alkyl, 1–4C-alkoxy or halogen, R8 is hydrogen, 1–4C-alkyl, 1–4C-alkoxy or halogen, R9 is hydrogen or 1–4C-alkyl, A is 1–7C-alkylene, 2–7C-alkenylene, 3–7C-cycloalkylene or phenylene, G is hydrogen, 1–7C-alkyl, 1–4C-alkyl which is completely or mainly substituted by fluorine, 2–7C-alkenyl, 3–7C-cycloalkyl, a mono- or di-1–4C-alkylcarbamoyl or -thiocarbamoyl radical, an N-1–4C-alkyl-N'-cyanoamidino radical, a 1-N-1–4C-alkylamino-2-nitroethylene radical, an N-2-propynyl-N'-cyanoamidino radical, an aminosulfonylamidino radical, the radical —N(R10)R11, the part of the compound of the above formula I bonded to A (including X and via X) or a cyclic system or bicyclic system which is unsubstituted or substituted by R12 and R13 and which is selected from the group consisting of benzene, naphthalene, furan, thiophene, pyrrole, oxazole, oxazoline, isoxazole, thiazole, thiazoline, isothiazole, imidazole, imidazoline, pyrazole, triazole, tetrazole, thiadiazole, thiadiazole 1-oxide, oxadiazole, pyridine, pyridine N-oxide, pyrimidine, halopyrimidine, piperidine, triazine, pyridone, benzimidazole, imidazopyridine, benzothiazole, benzoxazole, quinoline and imidazopyridazine, in which R10 is 1–7C-alkyl, 3–7C-cycloalkyl or Ar-1–4C-alkyl and R11 is 1–7C-alkyl, 3–7C-cycloalkyl or Ar-1–4C-alkyl, where Ar is phenyl, furyl, naphthyl, tetrahydronaphthyl or phenyl which is substituted by R14, R15 and R16, or in which R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, thiomorpholine, indoline, 1,2,3,4-tetrahydroquinoline and 1,2,3,4-tetrahydroisoquinoline, where a substituted pyrrolidino radical is substituted by one or two identical or different substituents selected from the group consisting of 1–4C-alkyl, 1–4C-alkoxy, 1–4C-alkoxy-1–4C-alkyl, 1–4C-alkoxycarbonyl, 1–4C-alkylcarbonyloxy, hydroxy-1–4C-alkyl, hydroxyl and carboxyl, a substituted piperidino radical is substituted by one, two or three identical or different substituents selected from the group consisting of 1–4C-alkyl, 1–4C-alkoxycarbonyl, hydroxy-1–4C-alkyl, phenyl or phenyl-1–4C-alkyl, which is substituted by R14, R15 and R16, benzoyl, benzoyl substituted by halogen and carboxyl, a substituted piperazino radical can be substituted in the 2-, 3-, 5- or 6-position by a 1–4C-alkyl radical, and is substituted in the 4-position by a substituent selected from the group consisting of 1–4C-alkyl, 3–7C-cycloalkyl, 3–7C-cycloalkyl-1–4C-alkyl, 1–4C-alkoxycarbonyl-1–4C-alkyl and carbamoyl, a substituted morpholino radical is substituted by one or two identical or different 1–4C-alkyl radicals, a substituted thiomorpholino radical is substituted by one or two identical or different 1–4C-alkyl radicals or a carboxyl group, a substituted indolin-1-yl radical can be substituted in the 2- and/or 3-position by a carboxyl group or by one or two identical or different 1–4C-alkyl radicals, and can be substituted in the benzo moiety by one or two identical or different substituents selected from the group consisting of 1–4C-alkyl, halogen and nitro, a substituted 1,2,3,4-tetrahydroquinoline radical is substituted by one or two identical or different substituents selected from the group consisting of 1–4C-alkyl, 1–4C-alkoxycarbonyl and halogen, a substituted 1,2,3,4-tetrahydroisoquinoline radical is substituted by one or two identical or different substituents selected from the group consisting of 1–4C-alkyl, carboxyl and phenyl, R12 is hydrogen, 1–4C-alkyl, hydroxyl, 1–4C-alkoxy, halogen, nitro, guanidino, carboxyl, 1–4C-alkoxycarbonyl, 1–4C-alkyl substituted by R17, phenyl substituted by R14, R15 and R16 or —N(R18)R19, R13 is hydrogen, 1–4C-alkyl, hydroxyl, 1–4C-alkoxy, halogen or trifluoromethyl, R14 is hydrogen, 1–4C-alkyl, hydroxyl, 1–4C-alkoxy, 1–4C-alkylcarbonyl, halogen, trifluoromethyl, 1–4C-alkylamino or nitro, R15 is hydrogen, 1–4C-alkyl, hydroxyl, 1–4C-alkoxy, halogen or nitro, and R16 is hydrogen or trifluoromethyl, R17 is hydroxyl, 1–4C-alkoxy, carboxyl, 1–4C-alkoxycarbonyl or —N(R18)R19, where
- R18 is hydrogen, 1–4C-alkyl or —CO—R20 and
- R19 is hydrogen or 1–4C-alkyl, or where
- R18 and R19, together and including the nitrogen atom to which both are bonded, are a piperidino or morpholino radical,
- R20 is hydrogen, 1–4C-alkyl or 1–4C-alkoxy,
- X is O (oxygen), N-1–4C-alkyl, NH or S,
- Y is O (oxygen), N-1–4C-alkyl, NH, S, 1,4-piperazinylene or 1,4-piperidinylene,
- Z is O (oxygen), N-1–4C-alkyl, NH or S or CO,
- m is a number from 1 to 7,
- n is a number from 0 to 4,
- t is the number 0 or 1 and
- u is the number 0 or 1, or its salts.

3. A compound of the formula I as claimed in claim 1, in which
- R1, R2, R3, R4, R5, R6, R8 and R9 are hydrogen,
- R7 is 1–4C-alkyl or halogen,
- A is 1–7C-alkylene,
- G is hydrogen, 1–4C-alkyl which is completely or mainly substituted by fluorine, the radical —N(R10)R11 or a cyclic system which is unsubstituted or substituted by R12 and R13 and which is selected from the group consisting of benzene, furan, thiophene, oxazole, oxazoline, oxazolidinone thiazole, imidazole, triazole, tetrazole, pyridine, pyrimidine, chloropyrimidine, piperidine and imidazopyridazine, in which
- R10 and R11, together and including the nitrogen atom to which both are bonded, are an unsubstituted or substituted 5- or 6-membered ring hetero(bi)cyclic system which is selected from the group consisting of pyrrolidine, piperidine, piperazine, morpholine, 1,2,3,4-tetrahydroquinoline and 1,2,3,4-tetrahydroisoquinoline, where
- a substituted piperazino radical is substituted in the 4-position by a substituent selected from the group consisting of 1–4C-alkyl and carbamoyl,
- R12 is hydrogen, 1–4C-alkyl, hydroxyl, halogen, nitro, carboxyl, 1–4C-alkoxycarbonyl or 1–4C-alkyl substituted by R17,
- R13 is hydrogen or 1–4C-alkyl,
- R17 is 3–7C-cycloalkyl or pyridinyl,
- X is O (oxygen), N-1–4C-alkyl or S,
- Y is O (oxygen), S or 1,4-piperazinylene,
- Z is O (oxygen) or S,
- m is a number from 1 to 4,
- n is a number from 0 to 2,
- t is the number 0 or 1 and
- u is the number 0 or 1, or its salts.

4. A compound of the formula I as claimed in claim 1, in which
- R1, R2, R3 R4, R5, R6, R8 and R9 are hydrogen,
- R7 is 1–4C-alkyl
- A is 2–4C-alkylene,
- G is hydrogen, 1–4C-alkyl which is completely or mainly substituted by fluorine or a cyclic system which is unsubstituted or substituted by R12 and R13 and which is selected from the group consisting of thiophene, oxazoline, oxazolidinone, imidazole, pyridine, pyrimidine and piperidine in which
- R12 is hydrogen, 1–4C-alkyl, hydroxyl, halogen, nitro or 1–4C-alkyl substituted by R17,
- R13 is hydrogen or 1–4C-alkyl,
- R17 is 3–7C-cycloalkyl or pyridinyl,
- X is O (oxygen) or S,
- Y is O (oxygen), S or 1,4-piperazinylene,
- Z is O (oxygen) or S,
- m is a number from 1 to 3,
- n is the number 0 or 1,
- t is the number 0 or 1 and
- u is the number 0 or 1, or its salts.

5. A compound of the formula I as claimed in claim 1, in which A is 2–7C-alkylene, X is S and Y is S, t is the number 1 and u is the number 0.

6. A compound of the formula I as claimed in claim 1, in which A is 2–7C-alkylene, X is O (oxygen) and Y is S, t is the number 1 and u is the number 0.

7. A compound of the formula I as claimed in claim 1, in which A is 2–7C-alkylene, X is O (oxygen), Y is O (oxygen), Z is S, t is the number 1 and u is the number 1.

8. A compound of the formula I as claimed in claim 1 which is selected from the group consisting of {3-Methyl-4-[2-(pyridin-4-ylmethylsulfanyl)-ethoxy]-pyridin-2-ylmethyl}-quinolin-3-yl-amine, (3-Methyl-4-{2-[2-(2-methyl-5-nitro-imidazol-1-yl)-ethylsulfanyl]-ethoxy})-pyridin-2-ylmethyl)-quinolin-3-yl-amine, (3-Methyl-4-{3-[2-(2-methyl-5-nitro-imidazol-1-yl)-ethylsulfanyl]-propoxy}-pyridin-2-ylmethyl)-quinolin-3-yl-amine, {3-Methyl-4-[3-(pyridin-2-ylmethylsulfanyl)-propylsulfanyl]pyridin-2-ylmethyl}-quinolin-3-yl-amine, {3-Methyl-4-[2-(pyridin-3-ylmethylsulfanyl)-ethoxy]-pyridin-2-ylmethyl}-quinolin-3-yl-amine and {3-Methyl-4-[2-(pyridin-2-ylmethylsuffanyl)-ethoxy]-pyridin-2-ylmethyl}-quinolin-3-yl-amine or its salts.

9. A pharmaceutical composition comprising a compound of the formula I as claimed in claim 1 and/or its pharmaceutically acceptable salts together with a pharmaceutically acceptable carrier.

10. A method for treating Helicobacter bacteria in a patient, comprising administering to said patient an effective amount of the compound of the formula I as claimed in claim 1 and/or its pharmaceutically acceptable salts.

* * * * *

UNITED STATES PATENT AND TRADEMARK OFFICE
CERTIFICATE OF CORRECTION

PATENT NO.    : 6,479,514 B1
DATED         : November 12, 2002
INVENTOR(S)   : Peter Zimmermann et al.

It is certified that error appears in the above-identified patent and that said Letters Patent is hereby corrected as shown below:

Column 40,
Line 41, please replace "Methyl-5-nitro-imidazol-l-yl)-ethylsulfanyl]-ethoxy)}-"
with -- Methyl-5-nitro-imidazol-l-yl)-ethylsulfanyl]-ethoxy}- --
Line 49, please replace "[2-(pyridin-2-ylmethylsuffanyl)-ethoxy]-pyridin-2-"
with -- [2-(pyridin-2-ylmethylsufanyl)-ethoxy]-pyridin-2- --

Signed and Sealed this

Fourth Day of March, 2003

JAMES E. ROGAN
*Director of the United States Patent and Trademark Office*